US012733926B2

(12) United States Patent
Blair et al.

(10) Patent No.: US 12,733,926 B2
(45) Date of Patent: Sep. 15, 2026

(54) FIBULAR FRACTURE STAPLE AND METHODS FOR USING THE SAME

(71) Applicant: MedShape, Inc., Atlanta, GA (US)

(72) Inventors: Jeremy Webster Blair, Atlanta, GA (US); Courtney Lynne Kline, Sandy Springs, GA (US)

(73) Assignee: MEDSHAPE, INC., Atlanta, GA (US)

(*) Notice: Subject to any disclaimer, the term of this patent is extended or adjusted under 35 U.S.C. 154(b) by 0 days.

(21) Appl. No.: 18/668,907

(22) Filed: May 20, 2024

(65) Prior Publication Data

US 2024/0382193 A1 Nov. 21, 2024

Related U.S. Application Data

(60) Provisional application No. 63/503,146, filed on May 18, 2023.

(51) Int. Cl.
*A61B 17/064* (2006.01)
*A61B 17/00* (2006.01)
(Continued)

(52) U.S. Cl.
CPC ...... *A61B 17/0642* (2013.01); *A61B 17/0682* (2013.01); *A61B 2017/00867* (2013.01);
(Continued)

(58) Field of Classification Search
CPC ..... A61B 17/0642; A61B 17/10; A61B 17/56; A61B 17/84; A61B 17/844;
(Continued)

(56) References Cited

U.S. PATENT DOCUMENTS

| | | | |
|---|---|---|---|
| 262,635 | A | 8/1882 | Adams |
| 2,632,356 | A | 3/1953 | Thiel |

(Continued)

FOREIGN PATENT DOCUMENTS

| | | |
|---|---|---|
| CA | 19966 | 6/1955 |
| CA | 50730 | 1/1983 |

(Continued)

OTHER PUBLICATIONS

Barbella, Michael, "Enovis Expands DynaClip Family With Debut of New Staples. The procedure-specific staples combine strength with sustained dynamic compression for mid-foot and first MTP joint fusions." Retrieved Nov. 8, 2024. Retrieved from the Internet: https://www.odtmag.com/breaking-news/enovis-expands-dynaclip-family-with-debut-of-new-staples/. Jan. 17, 2023.

(Continued)

*Primary Examiner* — Marcela I. Shirsat
(74) *Attorney, Agent, or Firm* — Husch Blackwell LLP; Bryan D. Stewart

(57) ABSTRACT

The present disclosure relates to a staple including a first leg and a second leg connected to a bridge at a first end and a third leg and a fourth leg that are connected to the bridge in line along a central axis spanning a length of the bridge between the first leg and the second leg. In some embodiments, the first leg and the second leg are substantially parallel with one another at the first end. According to particular embodiments, the staple is configured to provide multi-planer forces as the staple attempts to return to a relaxed position from a deformed position. Such multi-planer forces may align or compress two or more bone fragments. The staple may also include a hole and/or a notch for receiving or connecting with a faster.

11 Claims, 21 Drawing Sheets

(51) Int. Cl.
*A61B 17/068* (2006.01)
*A61B 17/56* (2006.01)
*A61B 17/68* (2006.01)
*A61B 17/80* (2006.01)
*A61B 17/84* (2006.01)

(52) U.S. Cl.
CPC ..... *A61B 17/064* (2013.01); *A61B 2017/0641* (2013.01); *A61B 17/0644* (2013.01); *A61B 2017/0645* (2013.01); *A61B 2017/0646* (2013.01); *A61B 17/0684* (2013.01); *A61B 17/56* (2013.01); *A61B 2017/564* (2013.01); *A61B 17/68* (2013.01); *A61B 2017/681* (2013.01); *A61B 17/8004* (2013.01); *A61B 17/8061* (2013.01); *A61B 17/809* (2013.01); *A61B 17/844* (2013.01)

(58) Field of Classification Search
CPC ............ A61B 17/0682; A61B 17/8004; A61B 17/8061; A61B 17/809; A61B 17/8085; A61B 17/064; A61B 17/0644; A61B 17/068; A61B 17/0684; A61B 17/68; A61B 2017/00526; A61B 2017/00867; A61B 2017/0641; A61B 2017/0645; A61B 2017/0646; A61B 2017/564; A61B 2017/681; A61B 2017/0688; A61L 31/022; A61L 31/14; A61L 31/16; A61L 2400/16; A61L 2400/00; A61L 2430/02; A61L 2430/00
USPC ......... 606/75, 280, 282, 283, 284, 286, 281, 606/297, 298, 299, 300, 96–98, 104–105, 606/86 B, 86 R, 902, 907, 911
See application file for complete search history.

(56) References Cited

U.S. PATENT DOCUMENTS 2,867,807 A 1/1959 Anstett
D193,140 S 7/1962 Brown
3,499,359 A 3/1970 Yrjanainen
3,611,708 A 10/1971 Moore
D227,976 S 7/1973 Gerald
3,969,975 A 7/1976 Krol
4,175,555 A 11/1979 Herbert
4,269,180 A 5/1981 Dall
4,402,445 A 9/1983 Green
4,454,875 A 6/1984 Pratt
4,537,185 A 8/1985 Stednitz
D281,814 S 12/1985 Pratt
4,570,623 A 2/1986 Ellison
D286,442 S 10/1986 Korthoff
4,640,271 A 2/1987 Lower
4,887,601 A 12/1989 Richards
4,983,176 A 1/1991 Cushman
5,019,079 A 5/1991 Ross
5,366,479 A 11/1994 McGarry
5,454,814 A 10/1995 Comte
5,662,655 A 9/1997 Laboureau et al.
5,964,768 A 10/1999 Huebner
6,001,101 A 12/1999 Augagneur et al.
6,048,344 A 4/2000 Schenk
6,187,009 B1 2/2001 Herzog et al.
6,306,140 B1 10/2001 Siddiqui
6,319,254 B1 11/2001 Giet et al.
D484,032 S 12/2003 Del Re
6,887,243 B2 5/2005 Culbert
D574,956 S 8/2008 Grim
D586,915 S 2/2009 Grim et al.
7,708,738 B2 5/2010 Fourcault et al.
7,722,610 B2 5/2010 Mola et al.
7,731,738 B2 6/2010 Jackson et al.
7,794,483 B2 9/2010 Capanni
D625,417 S 10/2010 Fox
D625,591 S 10/2010 MacDonald et al.
8,267,975 B2 9/2012 Mccombs et al.
D691,720 S 10/2013 Cheney
D693,929 S 11/2013 Fagan et al.
8,623,060 B2 1/2014 Vlahos et al.
8,702,768 B2 4/2014 Tipirneni
D705,930 S 5/2014 Cheney
D706,927 S 6/2014 Cheney
D707,357 S 6/2014 Cheney
D717,951 S 11/2014 Cheney
9,011,505 B2 4/2015 Prandi et al.
9,095,338 B2 8/2015 Taylor
9,113,976 B2 8/2015 Cicoira et al.
9,402,624 B1 8/2016 Scott et al.
9,427,232 B2 8/2016 Gupta et al.
D773,665 S 12/2016 Cheney et al.
D773,666 S * 12/2016 Cheney ........................ D24/155
D775,336 S 12/2016 Shelton
D775,351 S 12/2016 Agarwal et al.
D777,329 S 1/2017 Montoya
D780,311 S 2/2017 Cheney
D782,674 S 3/2017 Nering
9,585,656 B2 3/2017 Taber et al.
9,675,395 B2 6/2017 Averous et al.
D804,666 S 12/2017 Guo et al.
9,861,413 B2 1/2018 Palmer et al.
D810,933 S 2/2018 Chrisman
9,901,338 B2 2/2018 Anderson
10,085,743 B2 10/2018 Roedl
10,105,134 B2 10/2018 Biedermann et al.
10,117,647 B2 11/2018 Cheney
10,307,156 B1 6/2019 Blair et al.
D856,509 S 8/2019 Lange et al.
D857,199 S 8/2019 Cheney et al.
10,383,625 B1 8/2019 Pirela-Cruz
10,420,547 B2 9/2019 Weiner et al.
D870,284 S 12/2019 Hollis et al.
10,568,627 B2 2/2020 Guo et al.
10,610,218 B2 4/2020 Palmer et al.
D883,482 S 5/2020 Majors
D886,299 S 6/2020 Cundiff
D891,618 S 7/2020 Cheney
D892,331 S 8/2020 Hollis et al.
D895,113 S 9/2020 Blair
10,779,816 B2 9/2020 Goldstein et al.
10,863,982 B2 12/2020 Wahl
10,987,101 B2 4/2021 Ducharme et al.
11,006,949 B2 5/2021 Daniel
11,020,110 B1 6/2021 Blair
11,116,499 B1 9/2021 Blair et al.
11,179,149 B2 11/2021 Hartegen
D939,704 S 12/2021 Bales et al.
11,291,488 B1 4/2022 O'Flaherty et al.
11,311,289 B1 4/2022 Ritz et al.
D952,855 S 5/2022 Robbins
11,317,951 B2 5/2022 Hollis
11,331,130 B1 5/2022 Lui et al.
D957,636 S 7/2022 Blair
D960,371 S 8/2022 Hollis
D961,081 S 8/2022 Sayger
11,523,820 B2 12/2022 Cheney et al.
D974,559 S 1/2023 Bairstow et al.
D980,051 S 3/2023 Nettleton
11,642,124 B2 5/2023 Maclure et al.
D988,856 S 6/2023 D'Ascanio
11,684,359 B2 6/2023 Biedermann et al.
11,707,309 B2 7/2023 Legay et al.
D1,003,436 S 10/2023 Reed et al.
D1,004,088 S 11/2023 Niver et al.
D1,009,269 S 12/2023 Blair et al.
11,844,557 B2 12/2023 Evans et al.
11,911,025 B1 2/2024 Blair et al.
11,911,026 B1 2/2024 Blair et al.
D1,017,034 S 3/2024 Coyne et al.
D1,017,038 S 3/2024 Bushko et al.
11,925,345 B2 3/2024 Goldstein et al.
11,937,808 B2 3/2024 Campbell et al.
D1,024,332 S 4/2024 Blair et al.

(56) References Cited

U.S. PATENT DOCUMENTS

D1,025,358 S 4/2024 Blair et al.
11,969,167 B2 4/2024 Hartdegen et al.
D1,034,989 S 7/2024 Chevrel
12,042,386 B2 7/2024 Cheney et al.
D1,050,432 S 11/2024 Niver et al.
D1,050,433 S 11/2024 Reed et al.
12,207,815 B1 1/2025 Blair et al.
D1,081,989 S 7/2025 Blair et al.
D1,108,953 S 1/2026 Wire et al.
D1,120,327 S 3/2026 Blair et al.
D1,125,549 S 5/2026 Koka et al.
2003/0021655 A1 1/2003 Durand et al.
2005/0277940 A1 12/2005 Neff
2006/0058802 A1 3/2006 Kofoed
2006/0084980 A1 4/2006 Melkent et al.
2006/0173461 A1 8/2006 Kay et al.
2006/0233628 A1 10/2006 Lee
2006/0264954 A1 11/2006 Sweeney et al.
2007/0260248 A1 11/2007 Tipirneni
2007/0270855 A1 11/2007 Partin
2007/0270906 A1 11/2007 Molz
2008/0147126 A1 6/2008 Tipirneni et al.
2008/0147127 A1 6/2008 Tipirneni et al.
2008/0161808 A1 7/2008 Fox
2008/0167666 A1 7/2008 Fiere
2008/0234763 A1 9/2008 Patterson et al.
2008/0319443 A1 12/2008 Focht et al.
2009/0062800 A1 3/2009 Shano
2009/0105768 A1 4/2009 Cragg et al.
2009/0157123 A1 6/2009 Appenzeller et al.
2010/0036430 A1 2/2010 Hartdegen et al.
2010/0063506 A1 3/2010 Fox et al.
2010/0076498 A1 3/2010 Tyber et al.
2010/0268285 A1 10/2010 Tipirneni et al.
2011/0034925 A1 2/2011 Tipirneni et al.
2011/0118842 A1 5/2011 Bernard
2012/0316607 A1 12/2012 Andre et al.
2013/0030437 A1 1/2013 Fox
2013/0046351 A1 2/2013 Schwappach
2013/0123863 A1 5/2013 Hollis et al.
2013/0184768 A1* 7/2013 McIff .................... A61B 17/68
606/301
2013/0231667 A1 9/2013 Taylor et al.
2013/0267956 A1 10/2013 Terrill et al.
2014/0018809 A1 1/2014 Allen
2014/0097228 A1 4/2014 Taylor
2014/0276830 A1 9/2014 Cheney
2014/0277516 A1 9/2014 Miller
2014/0309639 A1 10/2014 Averous
2014/0358187 A1 12/2014 Taber
2015/0133940 A1 5/2015 Palmer et al.
2015/0282819 A1 10/2015 Austin
2015/0313592 A1 11/2015 Coillard-Lavirotte et al.
2016/0000434 A1 1/2016 Cocaign et al.
2016/0030039 A1 2/2016 Seavey et al.
2016/0066907 A1 3/2016 Cheney et al.
2016/0135808 A1 5/2016 Anderson
2016/0183992 A1 6/2016 Huang et al.
2016/0199060 A1 7/2016 Morgan et al.
2016/0235460 A1 8/2016 Wahl
2016/0338697 A1 11/2016 Biedermann
2017/0065275 A1 3/2017 Cheney
2017/0181779 A1 6/2017 Leither
2017/0196608 A1 7/2017 Castaneda et al.
2017/0202552 A1 7/2017 Coleman
2017/0252036 A1 9/2017 Palmer
2017/0311948 A1 11/2017 Morgan
2017/0360489 A1 12/2017 Palmer et al.
2018/0008263 A1 1/2018 Goldstein
2018/0092677 A1 4/2018 Peterson et al.
2018/0153551 A1 6/2018 Jianxin
2018/0177538 A1 6/2018 Hansson
2018/0271521 A1 9/2018 Wahl
2018/0303529 A1 10/2018 Zastrozna
2018/0353172 A1 12/2018 Hartdegen
2019/0000451 A1 1/2019 Majors
2019/0029674 A1 1/2019 Cheney
2019/0046182 A1 2/2019 Krumme
2019/0046183 A1 2/2019 Hartdegen
2019/0105040 A1 4/2019 Gordon
2019/0117219 A1* 4/2019 Ritz .................. A61B 17/0642
2019/0133657 A1 5/2019 Orbay et al.
2019/0150921 A1 5/2019 Fonte
2019/0154070 A1 5/2019 Kargenian
2019/0192140 A1 6/2019 Ducharme
2019/0192160 A1 6/2019 Stamp
2019/0357951 A1 11/2019 Rogers
2020/0000465 A1 1/2020 Maclure
2020/0008807 A1 1/2020 Hollis
2020/0038076 A1 2/2020 Amis
2020/0197005 A1 6/2020 Daniel
2020/0229813 A1 7/2020 Seykora
2021/0068822 A1 3/2021 Wahl
2021/0228206 A1 7/2021 Cheney
2021/0298748 A1 9/2021 Campbell
2021/0386422 A1 12/2021 Maclure
2022/0117599 A1 4/2022 Fein
2022/0280197 A1 9/2022 Blair et al.
2022/0338869 A1 10/2022 Kobayashi
2022/0401136 A1 12/2022 Niver
2023/0000488 A1 1/2023 Palmer et al.
2023/0172647 A1 6/2023 Knight et al.
2023/0200809 A1 6/2023 Wahl
2023/0255623 A1 8/2023 Ritz
2023/0258214 A1 8/2023 Wang
2023/0270435 A1 8/2023 Fox
2023/0346369 A1 11/2023 Bushko et al.
2024/0099715 A1 3/2024 Blair et al.
2024/0180600 A1 6/2024 Taylor et al.
2024/0315696 A1 9/2024 Hannah et al.
2025/0072891 A1 3/2025 Glerum et al.
2025/0072914 A1 3/2025 Glerum et al.

FOREIGN PATENT DOCUMENTS

CA 132677 6/2010
CN 303149448 4/2015
CN 304907199 11/2018
CN 306788209 S 8/2021
EA 8038400-0001 S 7/2020
FR 19852850001 S1 2/1986
FR 976142 S 4/1998
FR 2874166 2/2006
FR 3008302 1/2015
GB 1035018 12/1986
GB 6014567 6/2017
GB 6352633 S 3/2024
GB 6352634 S 3/2024
GB 6352635 S 3/2024
HU D0600258 S 5/2008
IN 256120 S 3/2024
IN 410996-001 S 3/2024
JP D1083812 S 9/2000
JP D1132991 2/2002
JP D1504138 8/2014
KR 300967753.0000 8/2018
WO 2015026357 2/2015
WO 2017207922 12/2017
WO 2018148284 8/2018
WO 2019226248 11/2019
WO 2022010920 A1 1/2022

OTHER PUBLICATIONS

MedShape Inc., "MedShape Launches the DynaClip Forte NiTiNOL Bone Fixation System. The four-leg design is indicated for Lapidus fusion and other demanding applications." Retrieved Nov. 8, 2024. Retrieved from the Internet: https://www.odtmag.com/breaking-news/medshape-launches-the-dynaclip-forte-nitinol-bone-fixation-system/. Sep. 10, 2020.

(56) References Cited

OTHER PUBLICATIONS

International Search Report and Written Opinion received for PCT Patent Application No. PCT/US2024/030224, mailed on Sep. 3, 2024, 12 pages.
International Search Report and Written Opinion received for PCT Patent Application No. PCT/US2023/075457, mailed on Feb. 14, 2024, 14 pages.
Depuy Synthes, Bme Elite Continuous Compression Implant Product Overview. DePuy Synthes, 2017. Pamphlet.
Stryker, EasyClip Osteosynthesis Compression Staples. Stryker GMBH, Switzerland, 2015. Pamphlet.
Wright, Fuseforce Fixation System Surgical Technique. Wright Medical Group N.V., Oct. 25, 2018. Pamphlet.
Enovis DynaClip Staple, "DynaClip Delta™ and DynaClip Quattro™", Instagram Post, Retrieved from: https://www.instagram.com/enovisfootankle/reel/CqTUwBeOhQv/, Retrieved on: Jan. 8, 2026, Mar. 27, 2023, 1 page.
PediatrOS™ FlexTack™ Staple, Merete, Retrieved from: https://web.archive.org/web/20200925115907/https://mereteusa.com/details/pediatros-flextack/, Retrieved on: Jan. 6, 2026, Sep. 25, 2020, 1 page.
REFLEX® Nitinol Staples, Medlineunite, Retrieved from: https://web.archive.org/web/20210517203839/https://medlineunite.com/product/reflex-nitinol-staples/, Retrieved on: Jan. 6, 2026, May 17, 2021, 1 page.
Stryker Launches EasyFuse™ Dynamic Compression System for High-Demand Foot and Ankle Applications, Buisnesswire, Retrieved from: https://www.businesswire.com/news/home/20220525005329/en/Stryker-Launches-EasyFuse-Dynamic-Compression-System-for-High-Demand-Foot-and-Ankle-Applications, Retrieved on: Jan. 6, 2026, May 25, 2022, 1 page.
DynaNail Helix, "Active, Adaptive Healing for Foot & Ankle Fusion", Enovis, Retrieved from: https://enovis.com/sites/defaulUfiles/DynaNail-Helix-Sales-Sheet.pdf, (Year: 2022), Retrieved on Jun. 12, 2026, 2 pages.
IBS, "Mid and Hindfoot Screw System", In2Bones, Retrieved from: https://www.in2bones.com/BRO/ST-MHFScrews-EN-042014-P.pdf, (Year: 2014), Retrieved on Jun. 12, 2026, 20 pages.
Trimed, "Large Headless Screws: Surgical Technique", Retrieved from: https://www.trimedortho.com/wp-content/uploads/2018/05/LC-72-0002-002-REV-A-STM-LargeHeadlessScrews.pdf, (Year: 2018), Retrieved on Jun. 12, 2026, 4 pages.

* cited by examiner

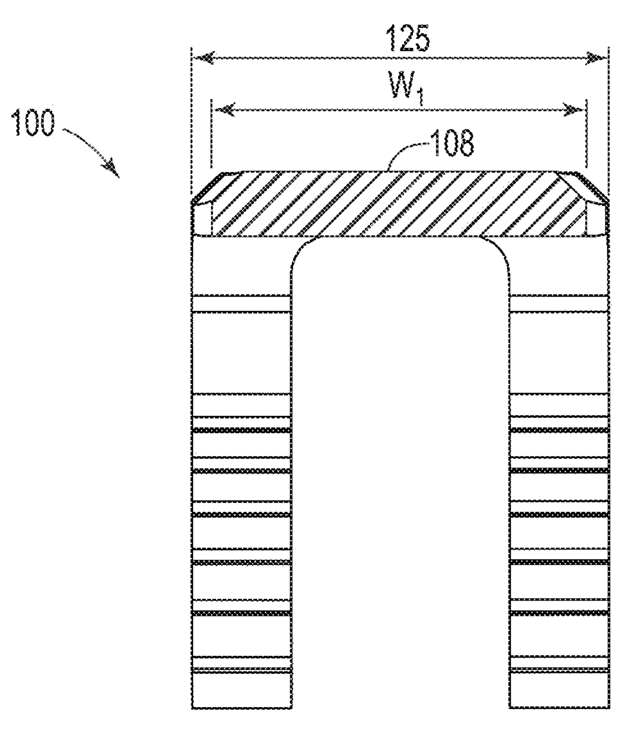
FIG. 1A
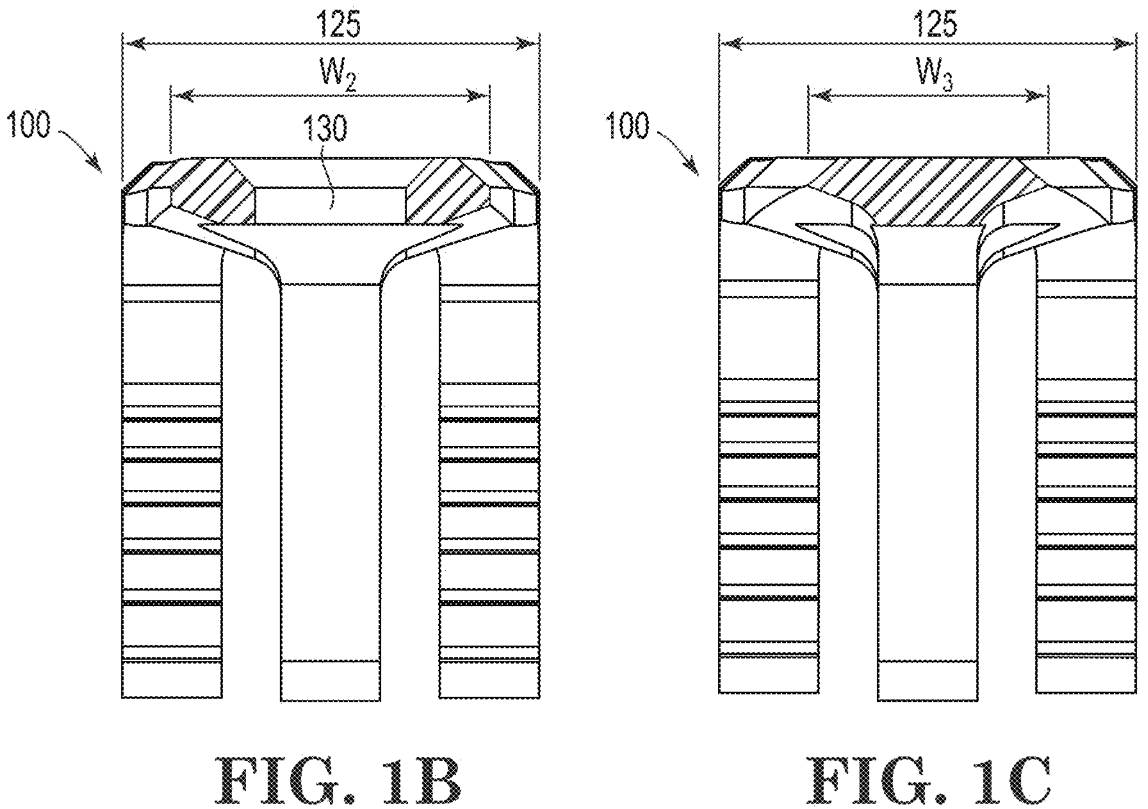
FIG. 1B
FIG. 1C

FIBULAR FRACTURE STAPLE AND METHODS FOR USING THE SAME

CROSS-REFERENCE TO RELATED APPLICATION(S)

This application claims priority to and the benefit of U.S. Provisional Patent App. Ser. No. 63/503,146 filed on May 18, 2023, entitled "FIBULAR FRACTURE STAPLE AND METHODS FOR USING THE SAME." The content of the aforementioned patent application is hereby expressly incorporated by reference in its entirety for all purposes.

BACKGROUND

Generally, surgical staples are used in some orthopedic applications for holding two bone segments together. Typically, segments of the same bone are separated (e.g., broken, fractured, etc.) and legs of a staple are inserted into each bone segment to compress ends of two (or more) segments of a broken bone together to promote healing of the bone (e.g., such that the bone segments heal back together).

TECHNICAL FIELD

The present disclosure relates generally to surgical staples configured for use in the treatment of fibular fractures (although other uses are contemplated), as well as processes for making and using the same. Specifically, embodiments of the present disclosure relate to a fibular fracture staple used in conjunction with syndesmotic screws that provide an advantageous alternative to other methods of fibular fracture reduction.

SUMMARY

In certain embodiments, a staple includes a first leg and a second leg connected to a bridge at a first end. The first leg and the second leg may be substantially parallel with one another at the first end. In at least one embodiment, the staple further includes a third leg and a fourth leg that are connected to the bridge in line along a central axis spanning a length of the bridge between the first leg and the second leg. In particular embodiments, the staple is configured to deform from a relaxed position to an active position, the relaxed position including at least one bend angle and at least one twist angle.

In certain embodiments, a method for connecting two or more bone fragments at an ankle joint is discussed herein.

According to a first aspect, the present disclosure includes a staple comprising: a first leg and a second leg connected to a bridge at a first end, wherein the first leg and the second leg are substantially parallel with one another at the first end; and a third leg and a fourth leg that are connected to the bridge in line along a central axis spanning a length of the bridge between the first leg and the second leg; wherein the staple is configured to deform from a relaxed position to an active position, the relaxed position comprising: a first bend angle between the first leg and a z-axis; a second bend angle between the second leg and the z-axis; a third bend angle between the third leg and the z-axis; a fourth bend angle between the fourth leg and the z-axis; a first torsion angle between the third leg and a y-axis; and a second torsion angle between the fourth leg and the y-axis; and wherein the staple is configured to align two or more bone fragments in the active position by exerting a force on the two or more bone fragments that is dependent upon the first bend angle, the second bend angle, the third bend angle, the fourth bend angle, the first torsion angle, and the second torsion angle.

In a second aspect of the staple of the first aspect or any other aspect, wherein, when the staple is in the relaxed position, at least one of the first bend angle, the second bend angle, the third bend angle, and the fourth bend angle are not equal to ninety degrees.

In a third aspect of the staple of the first aspect or any other aspect, wherein, when the staple is in the relaxed position, at least one of the first torsion angle and the second torsion angle are not equal to zero such that at least one of the third leg and the fourth leg are not perpendicular to the bridge.

In a fourth aspect of the staple of the first aspect or any other aspect, wherein one or more of the first leg, the second leg, the third leg, and the fourth leg comprise one or more teeth.

In a fifth aspect of the staple of the fourth aspect or any other aspect, wherein each of the first leg, the second leg, the third leg, and the fourth leg comprise one or more teeth.

In a sixth aspect of the staple of the fourth aspect or any other aspect, wherein each tooth comprises a tooth angle between an end of each tooth and a sloped surface of each tooth measuring between 45-60 degrees.

In a seventh aspect of the staple of the fourth aspect or any other aspect, wherein the one or more teeth comprise a terminal tooth at a distal end of at least one of the first leg, the second leg, the third leg, and the fourth leg.

In an eighth aspect of the staple of the fourth aspect or any other aspect, wherein the one or more teeth are positioned on an internal face of one or more of the first leg, the second leg, the third leg, and the fourth leg.

In a ninth aspect of the staple of the first aspect or any other aspect, wherein the bridge includes one or more holes configured to receive a fastener.

In a tenth aspect of the staple of the ninth aspect or any other aspect, wherein the one or more holes comprises a diameter between 1.5 millimeters to 5.5 millimeters.

In an eleventh aspect of the staple of the first aspect or any other aspect, wherein: the bridge comprises a top surface defining a curvature; a curvature angle is defined between the curvature and an x-axis; and the curvature angle is between zero and forty-five degrees.

In a twelfth aspect of the staple of the first aspect or any other aspect, wherein the bridge comprises a thickness measuring between 0.5-4.0 millimeters.

In a thirteenth aspect of the staple of the first aspect or any other aspect, wherein a cross-sectional width of the bridge varies continuously along the z-axis.

In a fourteenth aspect of the staple of the first aspect or any other aspect, wherein: the bridge comprises a top surface; the top surface includes one or more features; and the top surface includes one or more transition features between the one or more features.

In a fifteenth aspect of the staple of the first aspect or any other aspect, wherein the one or more transition features comprise a fillet, a chamfer, a blended surface, a loft, a sweep, or a blend curve.

According to a sixteenth aspect, the present disclosure includes a method for connecting two or more bone fragments at an ankle joint, the method comprising: making an incision on the ankle joint at a fracture site; securing the two or more bone fragments in a desired position; inserting a staple in a relaxed configuration into a surgical insertion tool to deform the staple to an active configuration; inserting the deformed staple in the active configuration into the two or more bone fragments; and allowing the staple to reform to the relaxed configuration.

According to a seventeenth aspect of the method of the sixteenth aspect or any other aspect, wherein the two or more bone fragments are secured in the desired position using one or more surgical clamping instruments.

According to an eighteenth aspect of the method of the sixteenth aspect or any other aspect, wherein the deformed staple in the active configuration is inserted into the two or more bone fragments using one or more screws.

According to a nineteenth aspect of the method of the eighteenth aspect or any other aspect, further comprising fastening the one or more screws through one or more apertures in the staple to the patient.

According to a twentieth aspect, the present disclosure includes a kit for connecting two or more bone fragments at an ankle joint, the kit comprising: a staple comprising: a first leg and a second leg connected to a bridge at a first end, wherein the first leg and the second leg are substantially parallel with one another at the first end; and a third leg and a fourth leg that are connected to the bridge in line along a central axis spanning a length of the bridge between the first leg and the second leg; wherein the staple is configured to deform from a relaxed position to an active position, the relaxed position comprising: a first bend angle between the first leg and a z-axis; a second bend angle between the second leg and the z-axis; a third bend angle between the third leg and the z-axis; a fourth bend angle between the fourth leg and the z-axis; a first torsion angle between the third leg and a y-axis; a second torsion angle between the fourth leg and the y-axis; and one or more apertures positioned through the bridge; one or more fasteners configured to interface with the staple at the one or more apertures to fasten into one or more bones.

According to a twenty-first aspect of the kit of the twentieth aspect or any other aspect, wherein the staple is configured to align two or more bone fragments in the active position by exerting a force on the two or more bone fragments that is dependent upon the first bend angle, the second bend angle, the third bend angle, the fourth bend angle, the first torsion angle, and the second torsion angle.

According to a twenty-second aspect of the kit of the twentieth aspect or any other aspect, wherein the one or more fasteners comprise at least one of one or more screws, one or more nails, one or more bolts, one or more rivets, and one or more pins.

According to a twenty-third aspect of the kit of the twentieth aspect or any other aspect, further comprising one or more staple guides for positioning the staple.

According to a twenty-fourth aspect of the kit of the twentieth aspect or any other aspect, further comprising a surgical stapler configured to apply the staple to a surgical site.

According to a twenty-fifth aspect of the kit of the twentieth aspect or any other aspect, further comprising one or more surgical tools for manipulating soft tissue at a surgical site.

According to a twenty-sixth aspect of the kit of the twenty-fifth aspect or any other aspect, wherein the one or more surgical tools comprise at least one of a scalpel, a tissue retractor, and a forceps.

According to a twenty-seventh aspect, a method comprising: inserting a surgical staple in an active configuration into one or more bony fragments of a patient; releasing the surgical staple from the active configuration, whereby the surgical staple applies multiplanar compression to the one or more bony fragments of the patient, wherein multiplanar compression is based at least in part on a twist angle and a bend angle of a bridge of the surgical staple.

Additional embodiments are described herein.

DETAILED DESCRIPTION OF THE FIGURES

The foregoing Summary and the following Detailed Description will be better understood when read in conjunction with the appended drawings. In the drawings:

FIGS. 1A-1C illustrate cross-sectional views of the exemplary staple of FIG. 1 taken at cross-sectional lines 1A, 1B, and 1C, respectively, along the x-axis.

DETAILED DESCRIPTION

Figure 1:
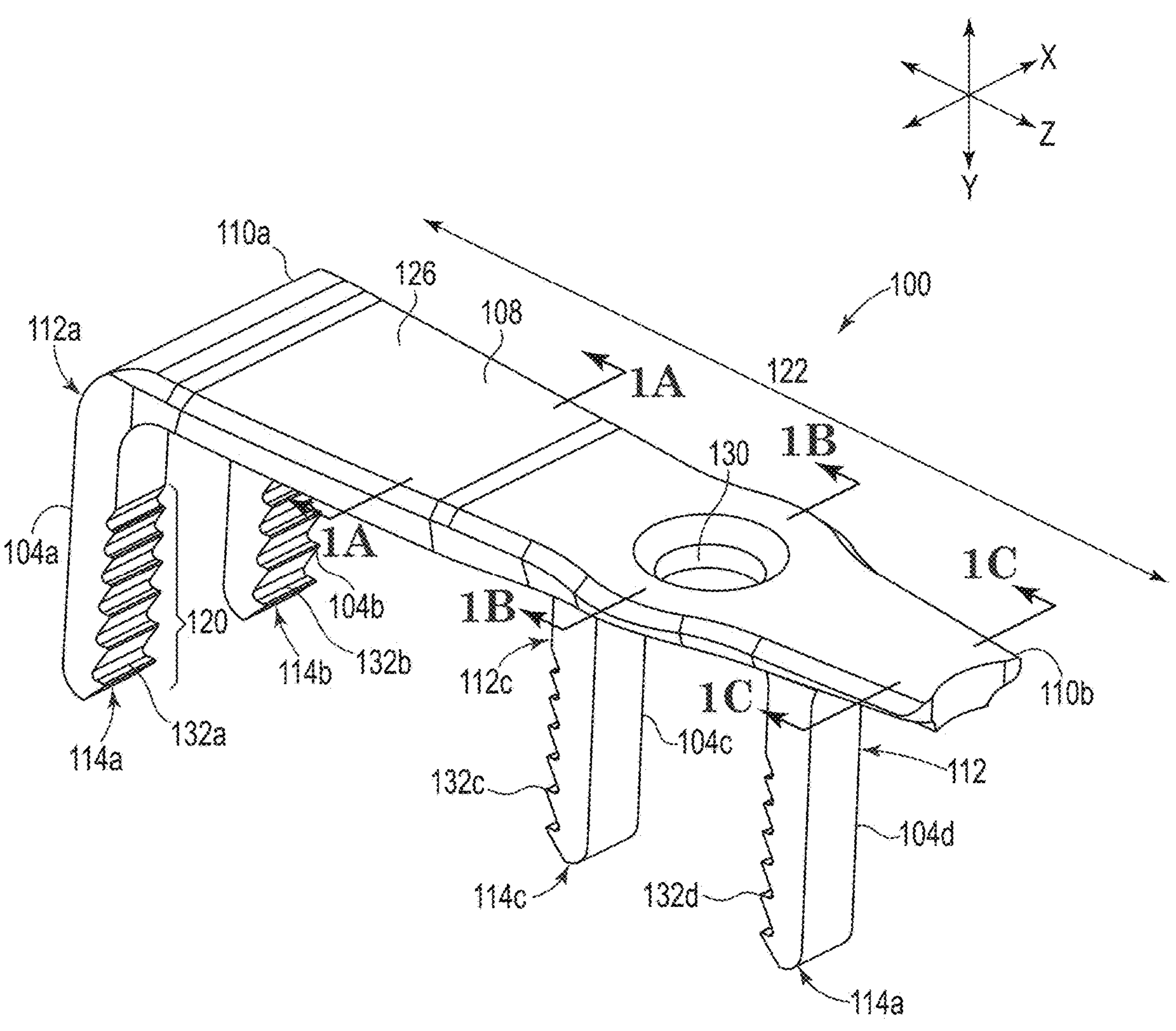
FIG. 1 illustrates a perspective view of an exemplary staple, according to one embodiment of the present disclosure.

The ankle joint (talocrural joint) comprises the talus fitting against the fibula and tibia in a mortise-lock joint type fit, and the distal tibio-fibular syndesmosis maintains stability of this joint during weight bearing activity by holding the tibia and fibula together. An injury such as a Weber fracture may result in a disruption to the syndesmosis and a separation of the tibia and fibula, causing a loosening of the talocrural joint. A Weber fracture may occur anywhere between a lower third of the fibula to the distal tip of the fibula (lateral malleolus), and may be categorized as Weber A, Weber B, and Weber C. In the case of a Weber B fracture, the fracture may be in line (trans-syndesmotic) with the distal tibio-fibular syndesmosis and thus reduce stability and weight bearing capacity of the overall ankle joint. Current methods of fracture fixation to the fibula include implantation of metal plates or a series of screws/nails to unite the fracture and rebind the tibia to the fibula but may present excessive bulk that may inhibit normal ankle function.

Generally, surgical staples are used in some orthopedic indications for holding two bone segments together. Typically, segments of the same bone are separated (e.g., broken, fractured, etc.) and legs of a staple are inserted into each bone segment to compress ends of two (or more) segments of a broken bone together to promote healing of the bone (e.g., such that the bone segments heal back together).

As will be understood, staples can compress bone segments together based on stored strain profiles of the staples. Such compression can limit the distance between broken bone segments, thereby possibly reducing bone healing time by eliminating gaps that need to be filled by the bones/body when healing. Further, such compression may help increase and accelerate bone growth.

The compressive properties of the staples described herein may be at least partially attributed to a selection of nitinol material. Nitinol, short for Nickel Titanium Naval Ordnance Laboratory, is a unique alloy renowned for its shape memory and superelastic properties. Composed primarily of nickel and titanium, Nitinol demonstrates the ability to revert to a predetermined shape when subjected to certain stimuli, such as temperature changes. In the medical field, Nitinol finds extensive application due to its biocompatibility, corrosion resistance, and its ability to withstand repeated deformations without loss of function. These properties make it ideal for various medical devices, including stents, guidewires, orthodontic wires, and surgical implants such as surgical staples.

In the realm of surgical staples, Nitinol offers several advantages over traditional materials like stainless steel. Nitinol's superelastic properties allow staples made from Nitinol to flex and conform to tissue, reducing the risk of trauma and enhancing patient comfort. Moreover, Nitinol staples may exert constant and uniform pressure on tissue, ensuring secure closure and minimizing the likelihood of complications such as bleeding or leakage. Additionally, Nitinol's shape memory properties enable staples to be pre-formed for easier deployment and accurate positioning during surgical procedures, contributing to improved surgical outcomes and reduced operative time. The pre-formed characteristics (such as the shape and structure of the staple) can contribute to distributing stress exerted on the Nitinol staple advantageously across a bridge of the staple to reduce breakage, as described below. These characteristics make Nitinol a desirable material for surgical staples, enhancing the efficiency and safety of various surgical interventions.

As will also be understood, space within the ankle joint is limited and lower profile staples may be desirable to the current methods of ankle fracture reduction. However, in creating a suitable low-profile fibular fracture staple (e.g., a staple that has minimum rise above the surface of a bone when the staple is fully inserted), the amount of stored strain (e.g., amount of compression the staple can impart when inserted) may be limited due to certain design constraints. Further, such staples may include localized strain concentrations (at corners and the like), which may increase risk of fatigue failure. Therefore, there exists a need for a cost-effective fibular fracture surgical staple that has the capacity for high sustained compression and that minimizes localized strain concentrations. Various embodiments of the present disclosure may utilize a staple having a low profile shape.

Aspects of the present disclosure generally relate to a fibular fracture staples that demonstrate constant moment of inertia between a deformed state and a non-deformed state. In various embodiments, the present staples demonstrate high sustained compression and improved fatigue performance (e.g., minimized localized strain concentrations), thereby mitigating any talar shift that may have occurred as a result of the fibular fracture and improving the weight bearing stability of the ankle joint.

As described herein, the staple is deformable between a first and a second position. Previous staples deform between first (e.g., relaxed) and second (e.g., active/deformed) positions by undergoing bending substantially at the connections between the staple bridge and staple legs; however, this approach may result in a large concentration of stress at the leg connections and, as a result, strain at the connections therebetween. The concentration of stress and strain at the transitions between the staple legs and staple bridge may reduce a durability of the staple and increase a likelihood of undesirable staple leg deformation or breakage. In at least one embodiment, the staple may bend or deform substantially along the bridge, thereby moving stress and strain concentrations from the transitions between the bridge and legs to the bridge itself. Thus, in one or more embodiments, the staples described herein overcome deficits of previous staples by concentrating staple bending in the staple bridge and providing a bridge top surface to distribute strain substantially equally throughout the bridge and to preserve a low profile nature of the staple.

As described herein, the disclosure includes, in certain embodiments, a surgical staple configured to deform from a relaxed position to an active position prior to insertion of the surgical staple. The surgical staple is then configured to store potential energy in its deformed, active state to exert one or more forces at a surgical site. In certain embodiments, these forces can be multiplanar forces (i.e., forces are exerted on one or more bones in one or more of the coronal, sagittal, and medial planes). It is desirable to utilize a surgical staple that exerts a multiplanar force on one or more bones at a fracture site to provide the ability to secure tissues with precise and consistent force in multiple planes. This multi-dimensional force application can ensure compression in a variety of directions (e.g., where it may not be possible to provide compression in each direction separately) and promote optimal healing, particularly in complex anatomical areas where traditional compression techniques or non-compressive devices may be less effective.

In certain embodiments, a multiplanar surgical staple can be used at an ankle joint to repair one or more bones in the ankle. In certain embodiments, the multiplanar surgical staple can be used outside of the ankle joint at other anatomical locations throughout the body. In certain embodiments, potential energy stored in the active (or deformed) state of the staple exerts a multiplanar force at an anatomical site as illustrated by any combination of the angles described below ($\theta_1$, $\theta_2$, $\theta_3$, $\theta_4$, $\theta_5$, $\theta_6$, $\theta_7$, $\theta_8$, $\theta_9$, $\theta_{10}$), which may be located between an axis (e.g., the x-axis, the y-axis, or the z-axis) and one or more features of the staple.

FIGS. 1-5 illustrate various views of an exemplary staple in deformed state, according to one embodiment of the present disclosure.

A legend is illustrated in FIG. 1 defining a z-direction along a length 122 of the example staple, a y-direction along a height 123 of the exemplary staple 100, and an x-direction along a width 125 of the exemplary staple 100. The same legend is used in other three-dimensional Figures, and a two-dimensional legend is used in Figures illustrating only two dimensions.

In certain embodiments, the exemplary staple 100 includes a bridge 108 spanning across a length 122 and at least two legs 104*a*, 104*b*, which may be integrally formed with the bridge 108. In some embodiments, the staple may include four legs 104*a*, 104*b*, 104*c*, 104*d*. A first and second leg 104*a*, 104*b* may be positioned at a first end 110*a* of the bridge 108. In one embodiment, the bridge 108 includes a substantially smooth top surface 126 including one or more shoulders 124*a*, 124*b*, 124*c*, 124*d* transitioning from the top surface 126 to an outer surface. Shoulders 124*a*, 124*b* may transition from the top surface 126 to an outer surface at the corresponding first and second leg 104*a*, 104*b* at the first end 110*a* of the bridge 108. A third leg 104*c* may be formed at a medial portion of the bridge 108 wherein a bottom surface 127 of the bridge 108 transitions to an outer surface of the corresponding third leg 104*c*. A fourth leg 104*d* may be formed proximate a second end 110*b* of the bridge 108 wherein the bottom surface 127 of the bridge 108 transitions to an outer surface of the corresponding fourth leg 104*d* and whereby a portion of the bridge 108 extends past the fourth leg 104*d* to the second end 110*b*. According to one embodiment, the staple size (e.g., bridge length×leg length) may be greater than, less than or equal to about 18.0 mm×20.0 mm.

In various embodiments, the first and second legs 104*a*, 104*b* may be substantially parallel at the first end 110*a* of the bridge 108. The third and fourth legs 104*c*, 104*d* may be substantially in-line at the medial portion and second end of the bridge. In one or more embodiments, the parallel characteristic of the first and second legs 104*a*, 104*b* and the in-line characteristic of the third and fourth legs 104*c*, 104*d* may be maintained regardless of the deformation state of the staple. For example, the first and second legs 104*a*, 104*b* remain substantially parallel as the staple transitions to from the relaxed state (not shown in FIGS. 1-4) and the deformed state shown in FIGS. 1-4 (e.g., via bending substantially along the bridge).

In various embodiments, the legs 104*a*, 104*b*, 104*c*, 104*d* are integrally formed with the bridge. In at least one embodiment, each leg 104*a*, 104*b*, 104*c*, 104*d* demonstrates a substantially rectangular cross-section. In other embodiments, the legs 104*a*, 104*b*, 104*c*, 104*d* may demonstrate any suitable shape (e.g., generally cylindrical, serpentine, obround, oval, tubular, etc.) and/or may differ from one another. In one or more embodiments, each leg 104*a*, 104*b*, 104*c*, 104*d* extends from the bridge 108 between a proximal end of the leg 112*a*, 112*b*, 112*c*, 112*d* and a distal end of the leg 114*a*, 114*b*, 114*c*, 114*d*. In various embodiments, the legs 104*a*, 104*b*, 104*c*, 104*d* are generally straight between the proximal end 112*a*, 112*b*, 112*c*, 112*d* and the distal end 114*a*, 114*b*, 114*c*, 114*d*. In some embodiments, one or more of the legs 104*a*, 104*b*, 104*c*, 104*d* demonstrate a concave or convex curvature between the proximal end 112*a*, 112*b*, 112*c*, 112*d* and the distal end 114*a*, 114*b*, 114*c*, 114*d*. In various embodiments, each leg 104*a*, 104*b*, 104*c*, 104*d* may include a length between the first and second ends of each leg 104*a*, 104*b*, 104*c*, 104*d* measuring at least about 12.0 mm, or about 12.0-24.0 mm, 12.0-14.0 mm, 14.0-16.0 mm, 16.0 mm, 16.0-18.0 mm, 18.0-20.0 mm, 20.0-22.0 mm, or 22.0-24.0 mm, or less than about 24.0 mm. In one or more embodiments, each leg 104*a*, 104*b*, 104*c*, 104*d* may include a thickness (e.g., between the outer surface and an inner surface) measuring at least about 0.5 mm, or about 0.5-6.0 mm, 0.5-1.0 mm, 1.0-2.0 mm, 2.0 mm, 2.0-3.0 mm, 3.0-4.0 mm, 4.0-5.0 mm, or 5.0-6.0 mm, or less than about 6.0 mm. In some embodiments, the thickness may taper between the proximal and distal ends of each leg.

In some embodiments, the shoulders 124*a*, 124*b* may have one or more radii that may be greater than, less than, or equal to about 0.50 mm to 1.50 mm. In particular embodiments, the shoulder 124 has one or more radii that may be greater than, less than, or equal to about 0.50 mm, 1.00 mm, 1.50 mm, 2.00 mm, or 2.50 mm.

In some embodiments, the shoulders 124*a*, 124*b* may have one or more radii that may be greater than, less than, or equal to about 0.50 mm to 1.50 mm. In particular embodiments, the shoulders 124*a*, 124*b* have one or more radii that may be greater than, less than, or equal to about 0.50 mm, 1.00 mm, 1.50 mm, 2.00 mm, or 2.50 mm.

Figure 27:
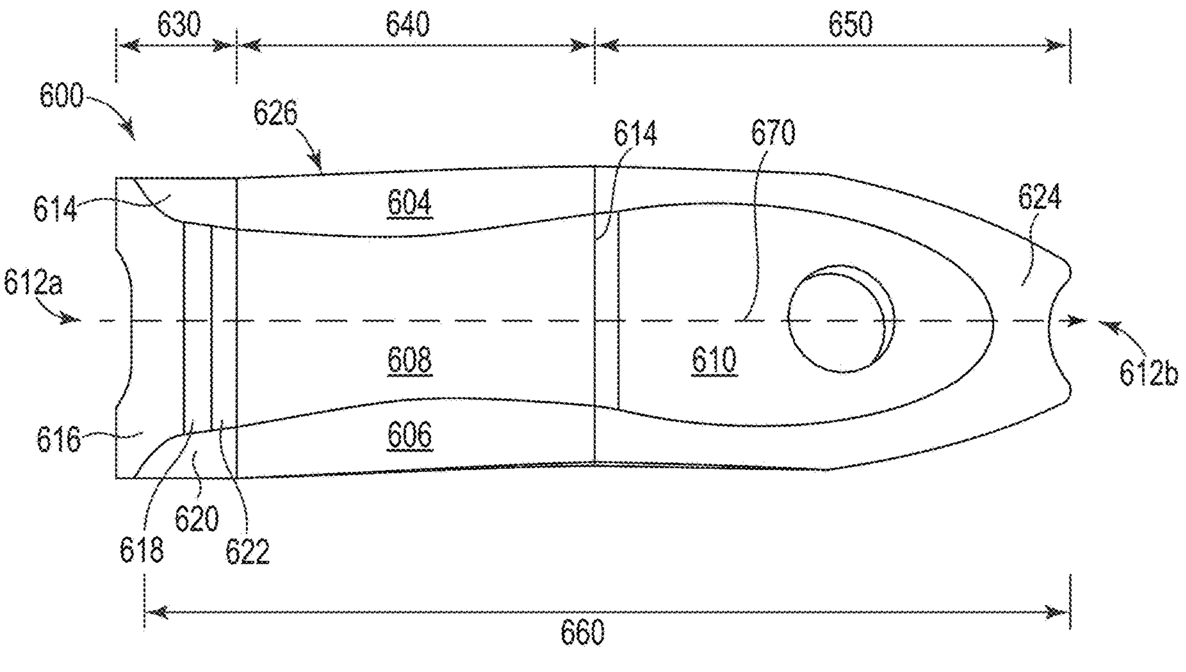
FIG. 27 illustrates a top view of the exemplary staple of FIGS. 22-26, according to one embodiment of the present disclosure.
Figure 28:
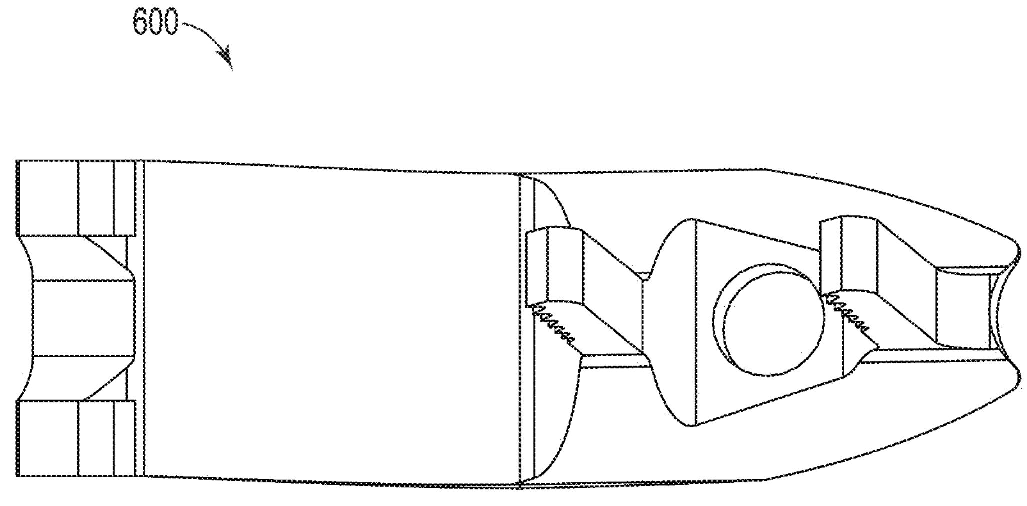
FIG. 28 illustrates a bottom perspective view of the exemplary staple of FIGS. 22-27, according to one embodiment of the present disclosure.

In some embodiments, midpoints of the third leg 104*c* and the fourth leg 104*d* are located at a midpoint of the bridge 108 (e.g., the legs are positioned along a centerline of the bridge; the centerline of the bridge is illustrated and described in further detail with respect to FIG. 27). In these embodiments (and others), a third shoulders 124*c* and a fourth shoulder 124*d* may connect the third leg 104*c* and the fourth leg 104*d* to the bridge with a slope, arch, or other transition from each edge of the bridge 108 to an edge of each of the legs 104*c* and 104*d*. In particular embodiments, the transition from the width of the bridge 108 to the depth of the legs 104*c* and 104*d* is substantially gradual and constant (e.g., a gradual slope or a constant radius arch). In some embodiments, the slope includes more than one slope of varying pitch or multiple arches of varying radii.

As shown in FIGS. 1-5, the bridge 108 is in an active position with a top surface 126 of the bridge 108 being substantially flat such that the top of surface of the bridge is substantially perpendicular to the y-axis. A staple shown in the undeformed or relaxed position is illustrated and described in further detail with respect to FIGS. 6-9.

In at least one embodiment, the bridge 108 includes substantially curved or radial transitions 140 between at least one of the legs, 104*a*, 104*b*, 104*c*, 104*d*, the one or more shoulders 124*a*, 124*b*, 124*c*, 124*d* and the bridge 108, resulting in the transfer of stress concentrations from undesirable regions (e.g., the connections between the staple bridge and staple legs) to more desirable regions (e.g., throughout the bridge 108). In certain examples, the curved or radial transitions between at least one of the legs, 104*a*, 104*b*, 104*c*, 104*d*, the one or more shoulders 124*a*, 124*b*, 124*c*, 124*d* and the bridge 108 is greater in width along the z-axis than the width of the legs 104*a*, 104*b*, 104*c*, 104*d*. In certain examples, the curved or radial transitions between at least one of the legs, 104*a*, 104*b*, 104*c*, 104*d*, the one or more shoulders 124*a*, 124*b*, 124*c*, 124*d* and the bridge 108 includes a fillet or chamfer, a blended surface, a loft, a sweep, or a blend curve. In certain embodiments, the substantially curved or radial transitions 140 are included at the third leg 104*c* and the fourth leg 104*d* to provide greater stability to the shoulders 124*c*, 124*d* and distribute forces from the legs 104*c*, 104*d* to the bridge 108.

In various embodiments, the movement of stress concentrations from undesirable to desirable regions advantageously reduces strain at the connections between the bridge 108 and the legs 104*a*, 104*b*, 104*c*, 104*d*, and, thus, reduces a likelihood of breakage between the bridge 108 and the legs 104*a*, 104*b*, 104*c*, 104*d*.

Figure 2:
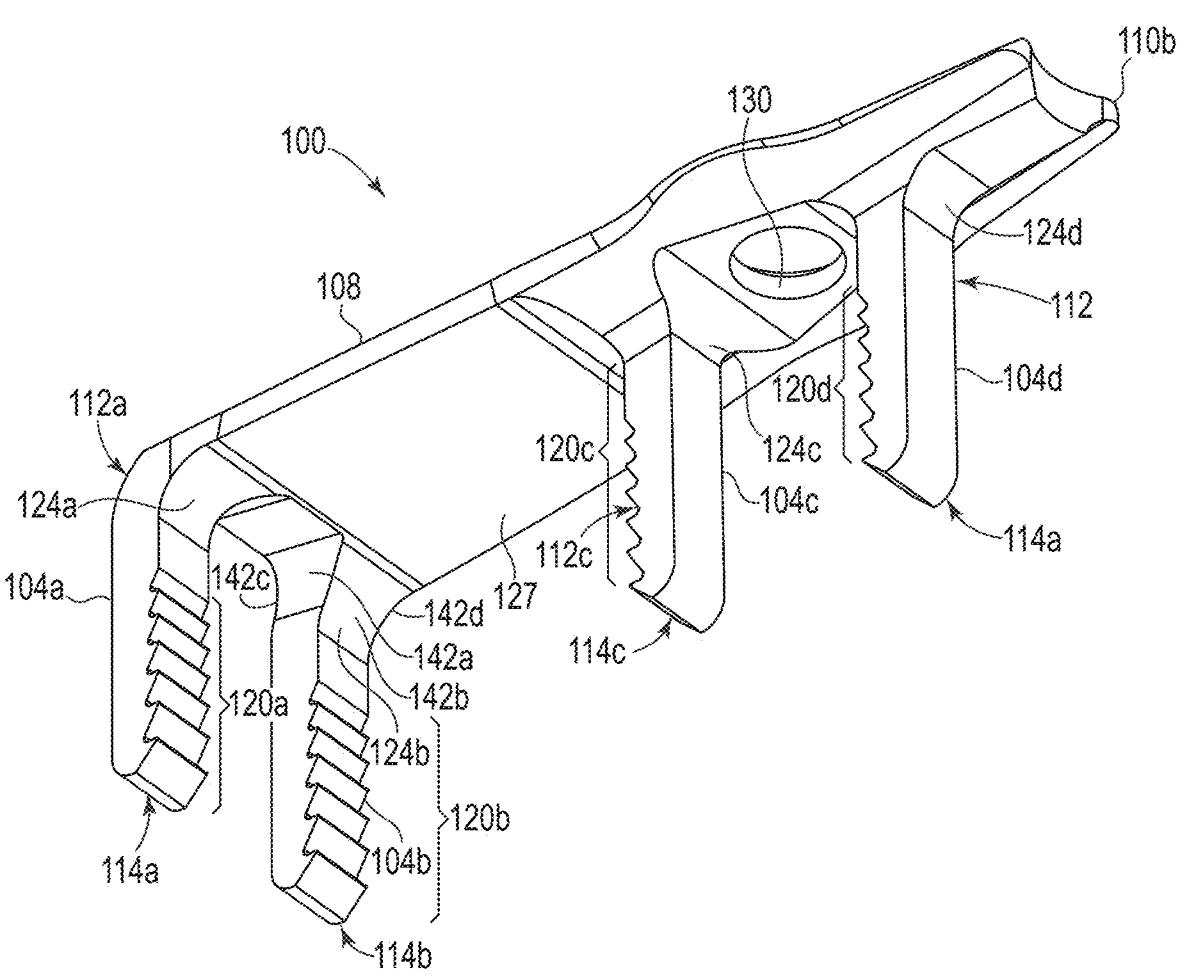
FIG. 2 illustrates a bottom perspective view of the exemplary staple of FIG. 1, according to one embodiment of the present disclosure.
Figure 3:
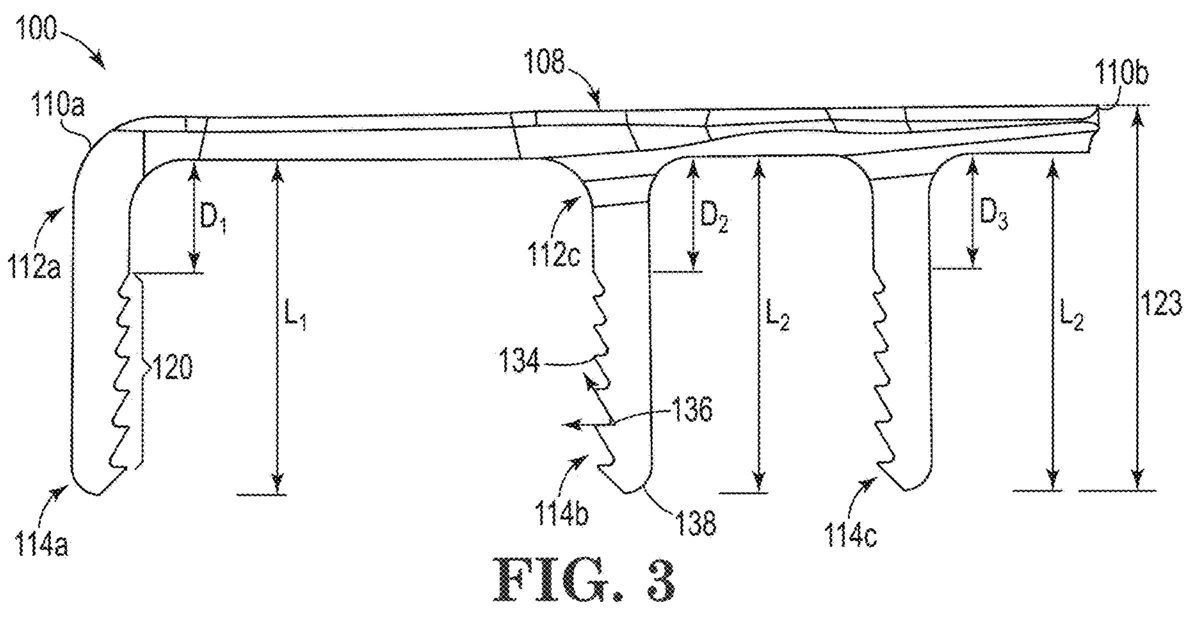
FIG. 3 illustrates a front view of the exemplary staple of FIGS. 1-2, according to one embodiment of the present disclosure.
Figure 4:
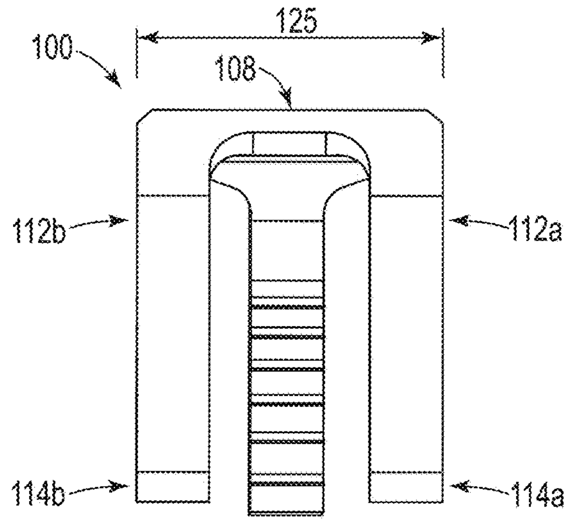
FIG. 4 illustrates a side view of the exemplary staple of FIGS. 1-3, according to one embodiment of the present disclosure.
Figure 5:
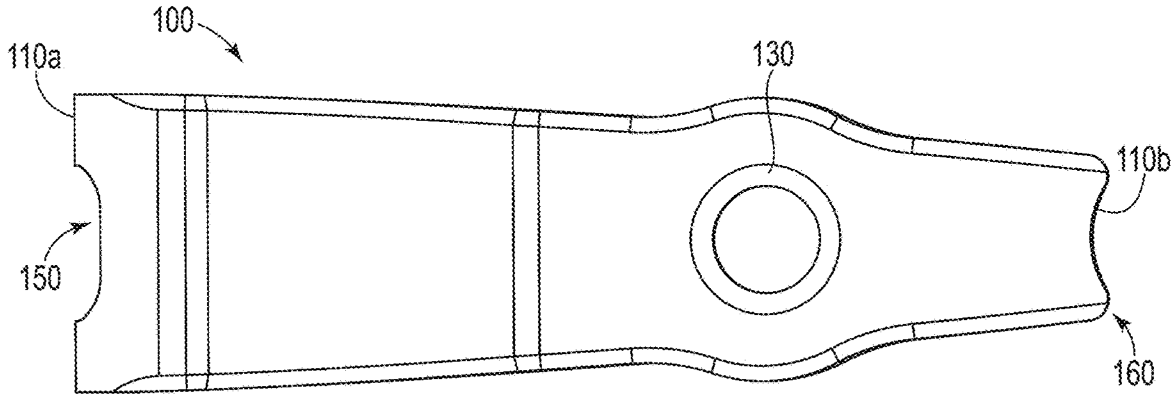
FIG. 5 illustrates a top view of the exemplary staple of FIGS. 1-4, according to one embodiment of the present disclosure.
Figure 6:
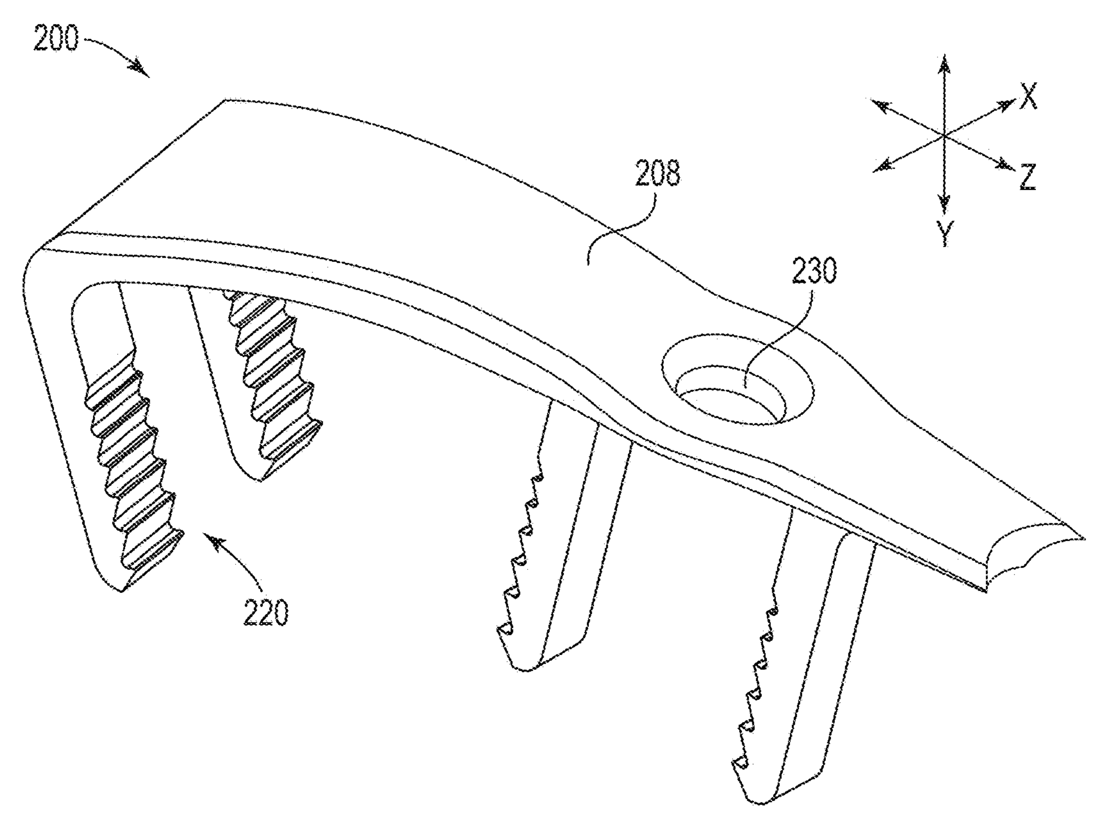
FIG. 6 illustrates a perspective view of an exemplary staple, according to one embodiment of the present disclosure.

In at least one embodiment, and as shown in FIG. 2, the bridge 108 may transition to each leg 104*a*, 104*b*, 104*c*, 104*d* at a shoulder 124*a*, 124*b*, 124*c*, 124*d*. The shoulder 124*a*, 124*b*, 124*c*, 124*d* can include first, second, third, and fourth side surfaces 142*a*, 142*b*, 142*c*, 142*d*. Furthermore, in certain embodiments, the bridge 108 can include one or more bridge side surfaces 144 for transitioning from the top surface 126 to the bottom surface 127. The transition between the top surface 126 and the side surfaces may be continuous, thereby promoting the equal distribution of stress throughout the bridge. In at least one embodiment, the side surfaces transition the bridge to the one or more shoulders and to the outer leg surface of the third and fourth legs.

In certain embodiments, the one or more bridge side surfaces 144 can vary in shape by including different lengths. In a non-limiting example, the bridge side surfaces 144 may include a maximum thickness at the first end 110*a* that gradually decreases to a thinner thickness toward the second end 110*b*. Having a maximum thickness of the bridge side surfaces 144 at the first end 110*a* and a minimum thickness at the second end 110*b* may be desirable to reduce or move stress concentrations and/or possible breakage points related to the twist, bend, or fixation (e.g., hole 130 and related screw insertion/force on the staple) features.

As shown in FIGS. 1-2, in various embodiments, the staple 100 includes one or more teeth sections 120*a*, 120*b*, 120*c*, 120*d*. In at least one embodiment, the teeth sections 120*a*, 120*b*, 120*c*, 120*d* are cut into each leg 104*a*, 104*b*, 104*c*, 104*d*. According to one embodiment, the teeth sections 120*a*, 120*b*, 120*c*, 120*d* include a plurality of teeth. In some embodiments, the teeth sections 120*a*, 120*b*, 120*c*, 120*d* are located on an internal face 132*a*, 132*b*, 132*c*, 132*d* (e.g., a face of each leg 104*a*, 104*b*, 104*c*, 104*d* that is positioned between two or more legs 104*a*, 104*b*, 104*c*, 104*d* along the length 122 of the bridge 108), of each of the legs 104*a*, 104*b*, 104*c*, 104*d*.

In various embodiments, the teeth sections 120*a*, 120*b*, 120*c*, 120*d* extend along the entire length L1, L2, L3, L4 of each leg 104. According to one embodiment, the teeth sections 120*a*, 120*b*, 120*c*, 120*d* extend along a partial length of the legs 104*a*, 104*b*, 104*c*, 104*d* with a distance D1, D2, D3, D4 along the legs not containing any teeth (also defining a length of each teeth sections 120*a*, 120*b*, 120*c*, 120*d* equal to the length of each leg (L1, L2, L3, L4) minus the distance that does not contain any teeth (D1, D2, D3, D4). The length of the teeth sections 120*a*, 120*b*, 120*c*, 120*d* may vary between each of the four legs 104*a*, 104*b*, 104*c*, 104*d*. In various embodiments, the teeth sections 120*a*, 120*b*, 120*c*, 120*d* demonstrates a wedge, curved, or straight shape, or any combination thereof. In one or more embodiments, a teeth sections 120*a*, 120*b*, 120*c*, 120*d* of each of the legs 104*a*, 104*b*, 104*c*, 104*d* may demonstrate a different (or the same) number of teeth such as, but not limited to, 4, 6, 8, 10, 14, 16, 18, or 20 teeth (and including values therebetween).

In at least one embodiment, each tooth 134 includes a tooth angle 136 between an end of each tooth and a sloped surface of each the tooth measuring at least about 45.0 degrees, or about 45.0-60.0 degrees, about 45.0 degrees, about 45.0-48.0 degrees, about 44.0-48.0 degrees, about 48.0-52.0 degrees, about 52.0-56.0 degrees, about 56.0-60.0 degrees, about 60.0 degrees, or less than about 60.0 degrees. In at least one embodiment, the teeth section includes a terminal tooth 138 toward the end of each leg. The terminal tooth 138 may be substantially similar to other teeth of the teeth section.

In one or more embodiments, the terminal tooth may define a shape of the tip (e.g., the terminal tooth defines a wedge shape of the tip). The tip that may define the distal end of the leg. The tip may include any suitable shape (e.g., points, rounded edges, blocked edges, chamfered edges, beveled edges, etc.) or combination of suitable shapes. According to one embodiment, the tip includes a wedge-shape for improving ease guiding and inserting the staple into a target site. In some embodiments, the tip tapers toward the second end of the leg. In at least one embodiment, the tip is blunted. For example, the tip demonstrates a generally rectangular or cylindrical shape of constant dimension (e.g., the tip is not tapered).

In some embodiments, the bridge 108 may include one more holes 130 spanning from the top surface 126 to the bottom surface 127. In some embodiments, the bridge 108 may include a shape demonstrating convexity toward a center of the one or more holes 130 to accommodate the one or more holes 130 on the bridge from a top face to a bottom face. In certain embodiments, the shape demonstrating convexity in the center includes a recess or cavity designed to fit a screw. In some embodiments, the one or more holes 130 are sized and shaped to accommodate one or more holes that are drilled through the top surface 126 of the bridge 108. In one or more embodiments, the one or more holes 130 are sized and shaped to accommodate a screw having a 3.5 mm shank while allowing a tightrope suture button (such as a 3.7 millimeter tight rope suture button) to be positioned at and/or through the one or more holes 130. In other embodiments, the bridge 108 may comprise a continuously smooth top surface 126 with no screw hole.

In some embodiments, other methods of fastening the staple 100 to the surgical site of the patient can be used without the one or more holes 130 and a screw. Certain methods of fastening the staple 100 to the surgical site of the patient may include, by non-limiting example, a biocompatible adhesive, a suture, a metal or plastic clip, or the use of another fastener such as a nail, a bolt, a rivet, or pin.

In some embodiments, a portion of the top surface 126 transitioning to the one or more holes 130 may form a "scalloped" indentation. The one or more holes 130 may be sized to receive one or more syndesmotic (or other types of) screws that may provide a method of compressional fixation of the staple to the underlying patient fibula and/or tibia. In various embodiments, the one or more holes may include a diameter measuring at least about 3.5 mm, or about 1.5-2.5 mm, 2.0-3.0 mm, 2.5-3.5 mm, 3.0-4.0 mm, 3.5-4.5 mm, 4.0-5.0 mm, or 4.5-5.5 mm, or less than about 5.5 mm. In some embodiments, the hole may be positioned 2.0-6.0 mm over the tibial plateau. As shown in FIGS. 1, 1A, 1B, and 1C, in various embodiments, the width 125 of the exemplary staple 100 varies along the length 122 of the exemplary staple 100. Cross-sectional lines 1A, 1B, and 1C shown in FIG. 1 illustrate a location of the cross-sections shown in FIGS. 1A, 1B, and 1C, respectively.

FIG. 1A shows a cross-sectional view along a width 125 of the exemplary staple 100 taken at cross-sectional line 1A shown in FIG. 1. A first cross-sectional width $W_1$ is shown spanning across at least a portion of the width 125 of the bridge 108. In certain embodiments, the first cross-sectional width $W_1$ is greater than the second cross sectional width $W_2$ and the third cross sectional width $W_3$.

FIG. 1B shows a cross-sectional view along a width 125 of the exemplary staple 100 taken at cross-sectional line 1B shown in FIG. 1. A second cross-sectional width $W_2$ is shown spanning across at least a portion of the width 125 of the bridge 108. In certain embodiments, the second cross-sectional width $W_2$ is less than the first cross sectional width $W_1$ and greater than the third cross sectional width $W_3$.

FIG. 1C shows a cross-sectional view along a width 125 of the exemplary staple 100 taken at location 1C shown in FIG. 1. A third cross-sectional width $W_3$ is shown spanning across at least a portion of the width 125 of the bridge 108. In certain embodiments, the third cross-sectional width $W_3$ is less than the first cross sectional width $W_1$ and the second cross sectional width $W_2$.

In certain embodiments, the first cross-sectional width $W_1$, the second cross-sectional width $W_2$, and the third cross-sectional width $W_3$ vary continuously along the length 122 of the exemplary staple. In other words, where the cross-sectional widths $W_1$, $W_2$, $W_3$ vary continuously, gradual alterations in the width 125 are made such that the width 125 of the bridge 108 transitions smoothly along the length 122 of the bridge 108. In certain embodiments, the gradual alterations may occur through shaping or tapering, resulting in a seamless transformation between the cross-sectional widths $W_1$, $W_2$, $W_3$ along the length 122 of the bridge 108.

In certain embodiments, the width 125 of the bridge 108 may vary discretely along the length 122 of the bridge 108 as characterized by distinct variations or indentations along a transition of the bridge 108 between the bridge 108 and the one or more shoulders 124*a*, 124*b*, 124*c*, 124*d*. These indentations represent localized points where the width abruptly shifts, creating a series of discrete segments with varying dimensions. Such variations may be intentional, serving functional or aesthetic purposes.

In certain embodiments, the exemplary staple 100 includes an indented feature 160 at the second end 110*b*. The indented feature 160 may be sized to receive or interface with one or more screws along an outline of the indented feature when the one or more screws are received during installation (as illustrated and described in further detail with respect to FIG. 10.

As shown in FIG. 2, the bridge 108 may increase in thickness between legs 104*c* and 104*d*. In the embodiment shown, the bridge increases in thickness from an edge 144 along the bottom surface, then transitions to a flat surface proximate the hole 130. As will be understood, this additional thickness/material may add stability to the staple to compensate for forces exerted on staple related to insertion and use of a fixation member via hole 130.

FIGS. 6-9 illustrate various views of an exemplary staple in the relaxed state, according to one embodiment of the present disclosure.

In some embodiments and as discussed herein, the staple 100 may be deformable from a relaxed (or manufactured state) shown in FIGS. 6-9 to the active state shown in FIGS. 1-5. As will be understood, the staple 100 may be configured to be deformed via a surgical inserter tool and then the staple will attempt to return to the relaxed state upon implantation (as illustrated and described in further detail with respect to FIG. 10), providing compression to bony fragments. As shown in the relaxed configuration of FIGS. 6-9, the bridge 208 may include a curvature 218 along the length of the bridge 208 (as illustrated and described in further detail with respect to FIGS. 6-9.

As further discussed below, the bridge in the relaxed state shown in FIGS. 6-9 includes a at least one bend and at least one twist angle (relative to the planer bridge shown in FIGS. 1-5). As will be understood from discussions herein, this disclosure contemplates any type of multiplanar shape setting, which may include a staple as described herein or other forms (a plate, a screw, a nail, a combination of fixation devices, etc.). Further, in various embodiments, the devices discussed herein may include any suitable twist angle or angles, which may vary from 0-90 degrees (or any suitable angle between). Moreover, a combination of twist or multiple twists and bend angles may provide benefits and/or directional shape setting that may not be possible via a single twist or bend angle.

In a deformed configuration, the bridge may be flat along its length such that a bridge angles $\theta_4$ and $\theta_5$ are equal or near equal to zero (see additional description relating to a bridge angles $\theta_4$ and $\theta_5$ below). Once inserted or released from an inserter, the bridge 208 may reform to include at least a percentage of the relaxed torsion/curvature. In some embodiments, twisting/bending of the bridge may enable the bottom surface 127 to compress a patient fibula proximate a fracture site. Such a configuration may allow for multi-axis compression along the staple and perpendicular to a fracture resulting from bridge bending and twisting (e.g., via shape setting). In some embodiments, the bridge 208 may include a length measuring about 14.0 mm, or about 14.0-26.0 mm, 14.0-16.0 mm, 16.0-18.0 mm, 18.0 mm, 18.0-20.0 mm, 20.0 mm, 20.0-22.0 mm, 22.0-24.0 mm, or 24.0-26.0 mm. In some embodiments, the bridge may include a thickness measuring at least about 0.5 mm, or about 0.5-4.0 mm, 0.5-1.0 mm, 1.0-1.5 mm, 1.2 mm, 1.22 mm, 1.5 mm, 1.52 mm, 1.55 mm, 1.5-2.0 mm, 1.6 mm, 1.62 mm, 1.69 mm, 1.7 mm, 1.74 mm, 1.92 mm, 2.0 mm, 2.0-2.5 mm, 2.5-3.0 mm, 3.0-3.5 mm, or 3.5-4.0 mm, or less than about 4.0 mm. Generally, a longer bridge 208 may include additional contouring, thereby affecting relative spacing of the legs. A shorter bridge 208 may be more suitable for trans-syndesmotic fracture patterns.

In at least one embodiment, the bridge 208 demonstrates a substantially constant moment of inertia across an entire length thereof between the first end 110*a* and the second end 110*b*. According to one embodiment, the substantially constant moment of inertia provides for more equitable distribution of stress concentrations throughout the bridge as compared to stress concentration distribution of previous staple bridges (e.g., that include discontinuous moments of inertia). In various embodiments, the bridge is substantially twisted between the first end and the second end in the relaxed position. In at least one embodiment, the low profile geometry of the bridge contributes to improved stability amidst the torsional deformation of the bridge resulting from implantation, thus reducing a risk of the bridge 208 becoming caught on and/or disturbed by external surfaces.

Figure 7:
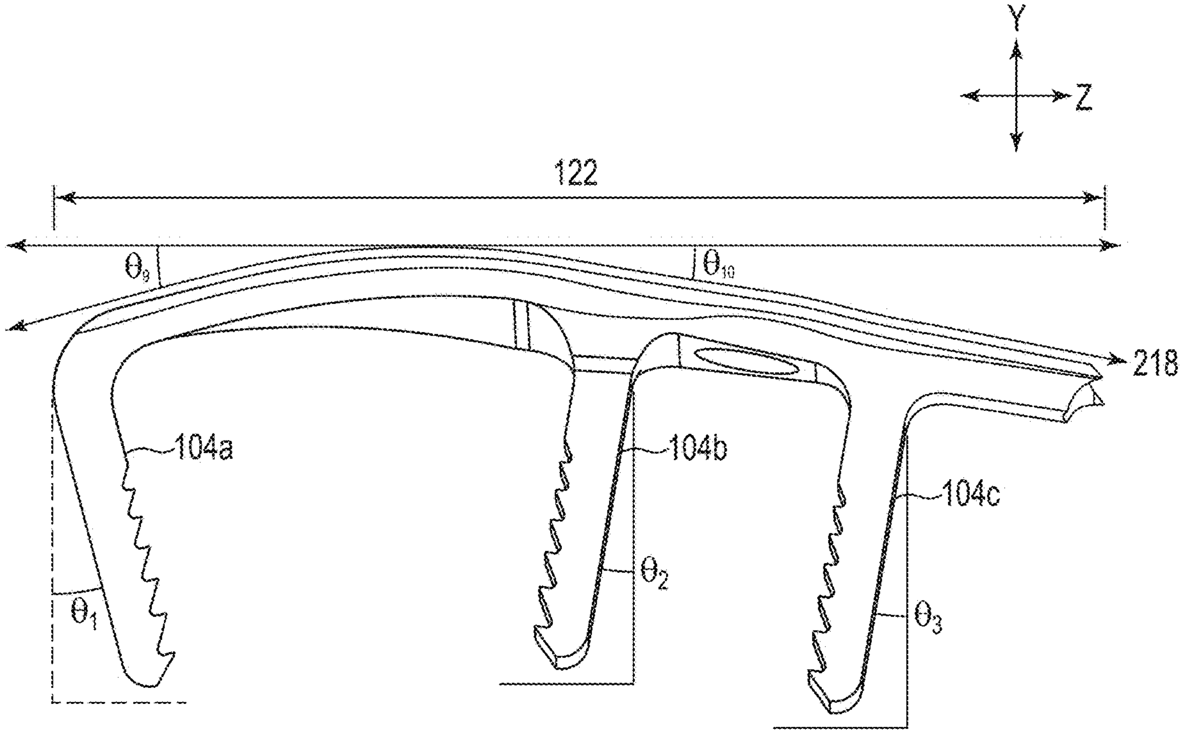
FIG. 7 illustrates a front view of the exemplary staple of FIG. 6, according to one embodiment of the present disclosure.

As shown in FIG. 7, the staple bridge 208 is manufactured/created with a bend relative to a plane along the z-axis. This bend creates one or more bend angles $\theta_1$, $\theta_2$, $\theta_3$ formed between the legs 104*a*, 104*b*, 104*c*, 104*d* and the y-axis. When the staple 200 having one or more bend angles $\theta_1$, $\theta_2$, $\theta_3$ is deformed (as shown in FIGS. 1-5) and inserted into a patient, the staple is configured to attempt to return from the active state to the relaxed state. As such, the exemplary staple 100 can exert a force on one or more bone fractures in one or more directions due to its inherent biomechanical properties. The one or more bend angles $\theta_1$, $\theta_2$, $\theta_3$ combined with the rigidity and elastic or superelastic properties of the staple material, enables the staple 100 to exert compressive forces perpendicular to its orientation within the bone. As the staple 100 is inserted and seated across the fracture site, the bend angle acts as a stabilizing mechanism, resisting movement and maintaining alignment and compression of the fractured bone fragments.

Moreover, the interaction between the staple 200 (which may represent staple 100 in the undeformed/related state), and the one or more bone fragments creates a biomechanical system where the force exerted by the staple 200 in one direction generates a reaction force in an opposing direction. This phenomenon, known as Newton's third law of motion, applies here, causing the staple to effectively compress the bone fragments together while simultaneously providing structural support to resist forces that may cause displacement or misalignment.

Additionally, the design of the staple, including its shape and dimensions, influences the distribution and magnitude of the forces exerted on the bone. By strategically manufacturing the staple with a bend and/or twist, surgeons can tailor the direction and magnitude of the compressive forces to optimize the healing process and promote bone fusion. This dynamic interaction between the staple and the bone tissue highlights the importance of precise surgical technique and implant selection in achieving successful fracture repair and patient recovery.

Furthermore, as shown in FIG. 7, an angle $\theta_9$ and an angle $\theta_{10}$ between the curvature 218 and the x-axis is shown (with a line denoting the x-axis placed at a highest point of the curvature 218 on the y-axis). The angle $\theta_9$ represents the angle between the curvature 218 and the x-axis from the highest point of the curvature on the y-axis toward the second end 214*b*. The angle $\theta_{10}$ represents the angle between the curvature 218 and the x-axis from the highest point of the curvature on the y-axis toward the first end 214*a*. In certain embodiments, the angles $\theta_9$ and $\theta_{10}$ are between 0-89 degrees. In certain embodiments, the angles $\theta_9$ and $\theta_{10}$ are between 0-30 degrees. In certain embodiments, the angles $\theta_9$ and $\theta_{10}$ are equal to 10 degrees The angles $\theta_9$ and $\theta_{10}$ can be equal to or unequal to each other.

Figure 9:
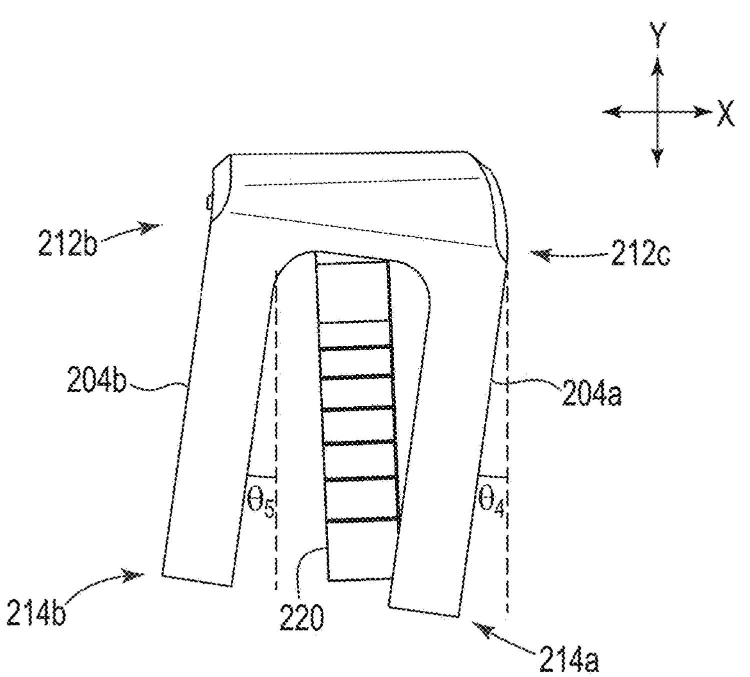
FIG. 9 illustrates a side view of the exemplary staple of FIGS. 6-8, according to one embodiment of the present disclosure.

As shown in FIG. 9, the twist of the bridge (which may be, e.g., approximately 10 degrees from planer) in the embodiment shown creates one or more torsional angles $\theta_5$, $\theta_6$ formed between at least one of the legs 104*a*, 104*b*, 104*c*, 104*d* and the y-axis. When the exemplary staple 200 having a torsional angle (in a direction perpendicular to the one or more bend angles $\theta_1$, $\theta_2$, $\theta_3$ described above) is inserted into a patient to heal bone fractures, it can exert a torque on the one or more bone fractures along the x-axis. The torsional angle, combined with the inherent stiffness of the staple material, enables the staple to resist rotational forces applied to the bone. As the staple is implanted across the fracture site, the one or more torsional angles of the device, represented by torsion angles $\theta_5$, $\theta_6$ act as a stabilizing mechanism, preventing excessive rotation or twisting of the bone fragments and/or pressing the distal end of the fibula towards the front of the foot/ankle joint for providing therapeutic benefits. In some embodiments, each of the legs 204*a*, 204*b*, 204*c*, 204*d* can include a torsional angle for applying a torque to the one or more bone fragments.

Figure 8:
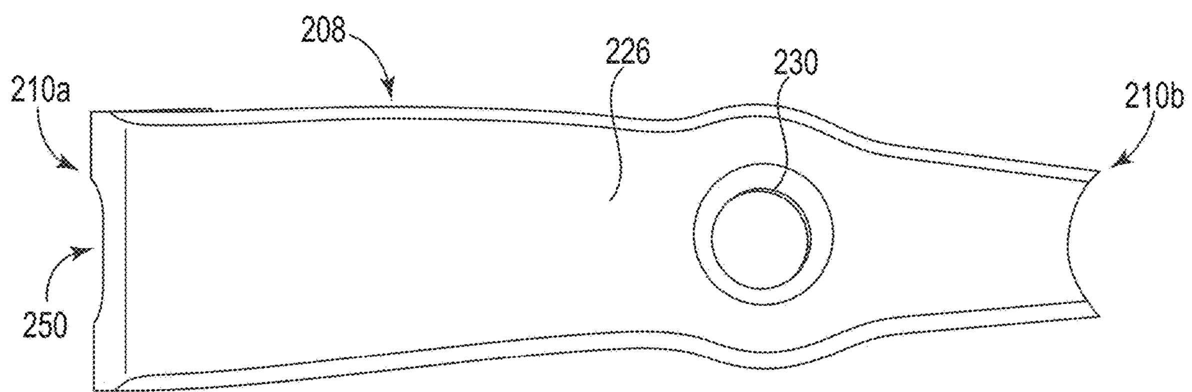
FIG. 8 illustrates a top view of the exemplary staple of FIGS. 6-7, according to one embodiment of the present disclosure.

According to some embodiments, and as shown in FIG. 8, the top surface 226 defines an indented ridgeline 250 along the first end 210*a* of the bridge 208. The indented ridgeline 250 can be include several unique advantages by reducing the amount of material in the staple, which may reduce a cost to produce the staple, provide greater flexibility and stress distribution along the bridge 208, and provide enhanced imaging visibility by providing distinct features that appear on X-ray or CT scans.

Figure 10:
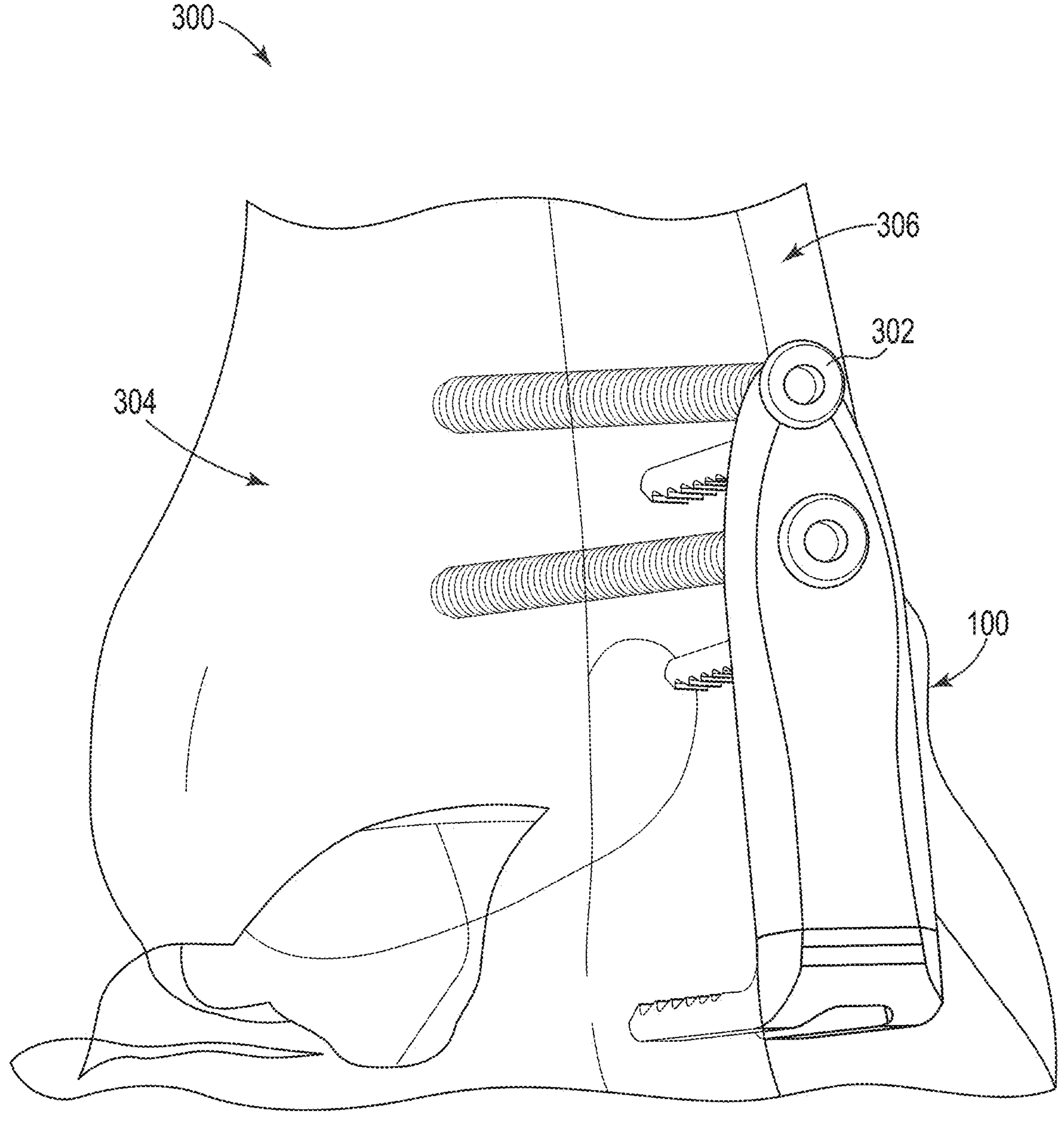
FIG. 10 illustrates a perspective view from a posterior end of the ankle joint showing an exemplary staple joining one or more bones of the ankle joint using a syndesmotic surgery procedure.
Figure 11:
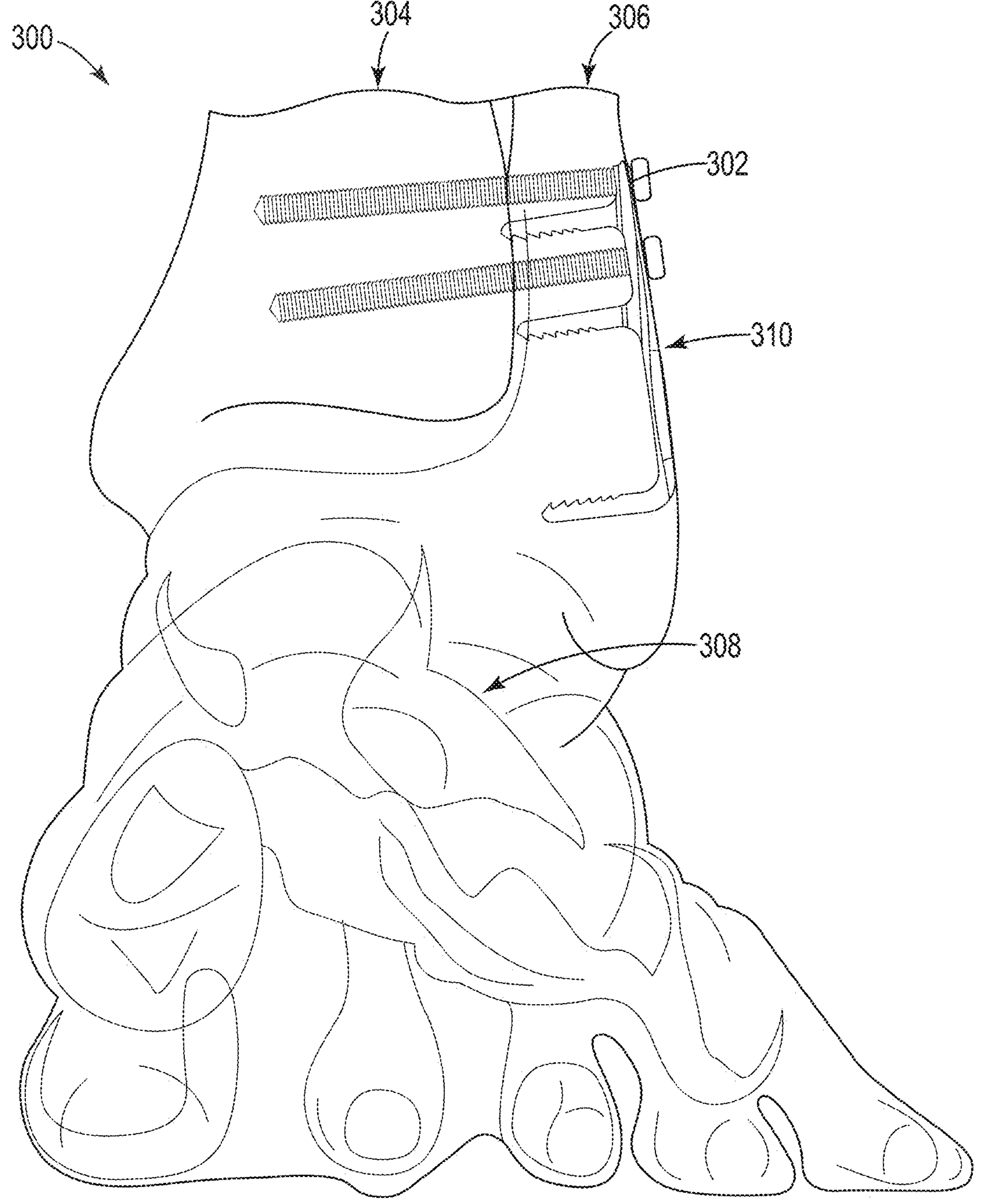
FIG. 11 illustrates a perspective view from an anterior end of the ankle joint showing an exemplary staple joining one or more bones of the ankle joint using a syndesmotic surgery procedure.

FIGS. 10-11 show various examples of surgical repairs of a weber fracture at an ankle joint 300. The ankle joint is generally formed by the tibia, fibula, and talus, which work together to provide stability, support, and flexibility to the foot to enable movements such as dorsiflexion and plantarflexion. The tibia (or shinbone) forms a medial portion of the ankle joint and bears most of the body's weight during weight-bearing activities. The fibula forms a lateral side of the ankle joint and provides lateral stability to the ankle joint. The talus sits atop the calcaneus (heel bone) and forms a lower part of the ankle joint that serves as the primary connection between the foot and the leg.

FIGS. 10-11 illustrate a distal tibio-fibular syndesmosis that provides stability to the ankle joint 300 by holding the tibia and fibula together. The exemplary staple 100 is inserted into the patient at the ankle joint 300. When the exemplary staple 100 is inserted into the patient in the deformed state (FIGS. 1-5), it attempts to move from the deformed state to an undeformed, or relaxed, state (as illustrated and described in further detail with respect to FIGS. 6-9).

In certain embodiments, the exemplary staple 100 is inserted into the ankle joint 300 by inserting the legs 104*a*, 104*b*, 104*c*, 104*d* into the fibula 306. Furthermore, in certain embodiments, one or more fasteners 302 (e.g., screws) can be used to fasten the exemplary staple 100 to the ankle joint 300 and connect the staple 100 to one or more bones within the ankle joint.

In some embodiments, and as shown in FIG. 10, the placement of the exemplary staple 100 can include, by non-limiting example, using the exemplary staple and the one or more fasteners 302 to stabilize the fibula 306 relative to the tibia 304 while providing compression to a fracture in the fibula to promote healing and bone growth.

In some embodiments, and as shown in FIGS. 10-11, the placement of the exemplary staple 100 can include, by non-limiting example, using the exemplary staple 100 and the one or more fasteners 302 to stabilize the fibula 306 relative to the tibia 304 in a syndesmotic procedure. By stabilizing the fibula 306 relative to the tibia 304, syndesmotic procedures help maintain proper alignment and function of the ankle joint 300, particularly in cases of syndesmotic injuries or fractures.

Figure 12:
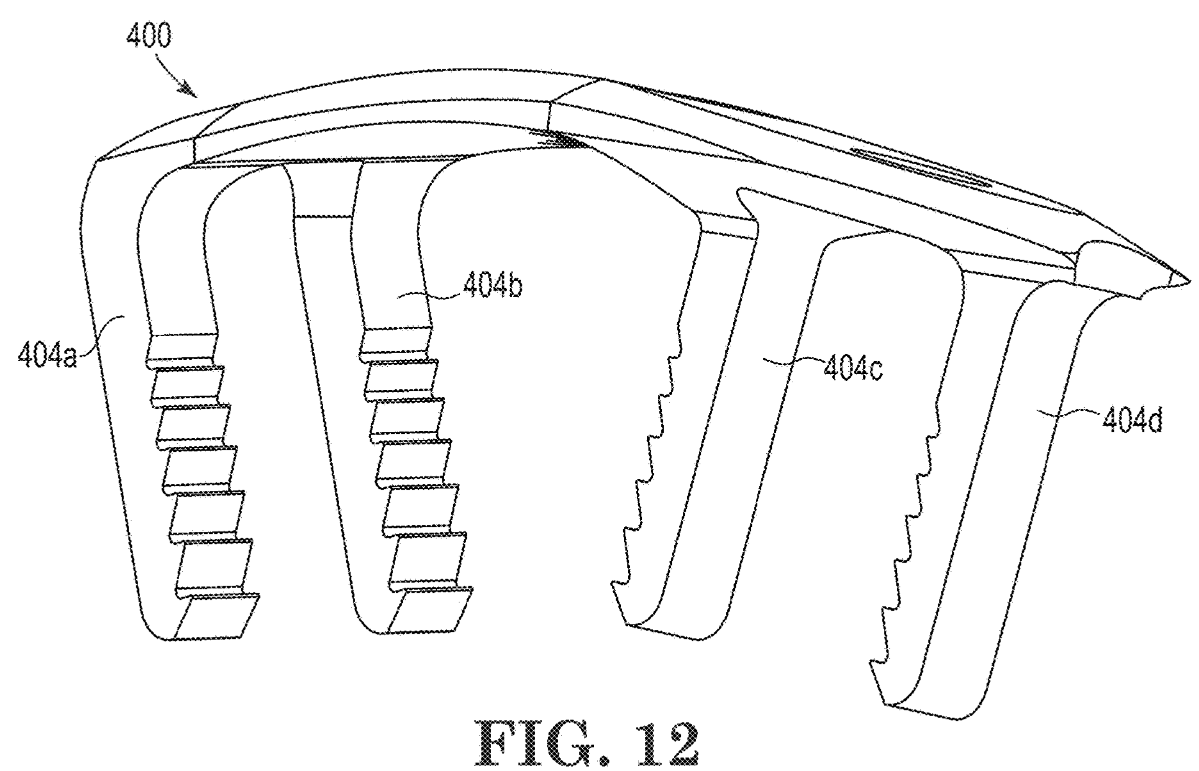
FIG. 12 illustrates a front perspective view of an exemplary staple, according to one embodiment of the present disclosure.
Figure 13:
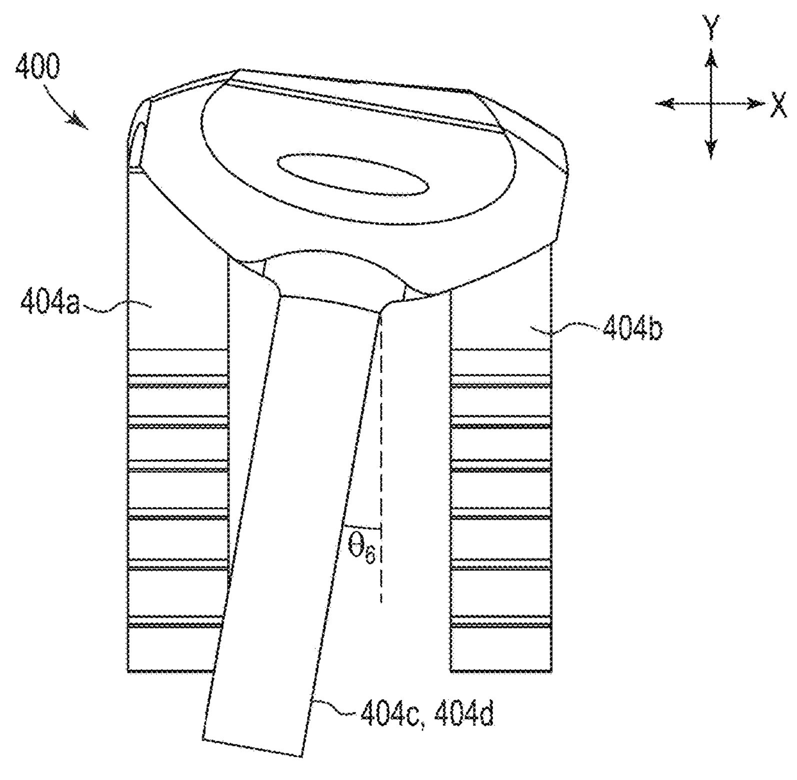
FIG. 13 illustrates a side view of an exemplary staple, according to one embodiment of the present disclosure.
Figure 14:
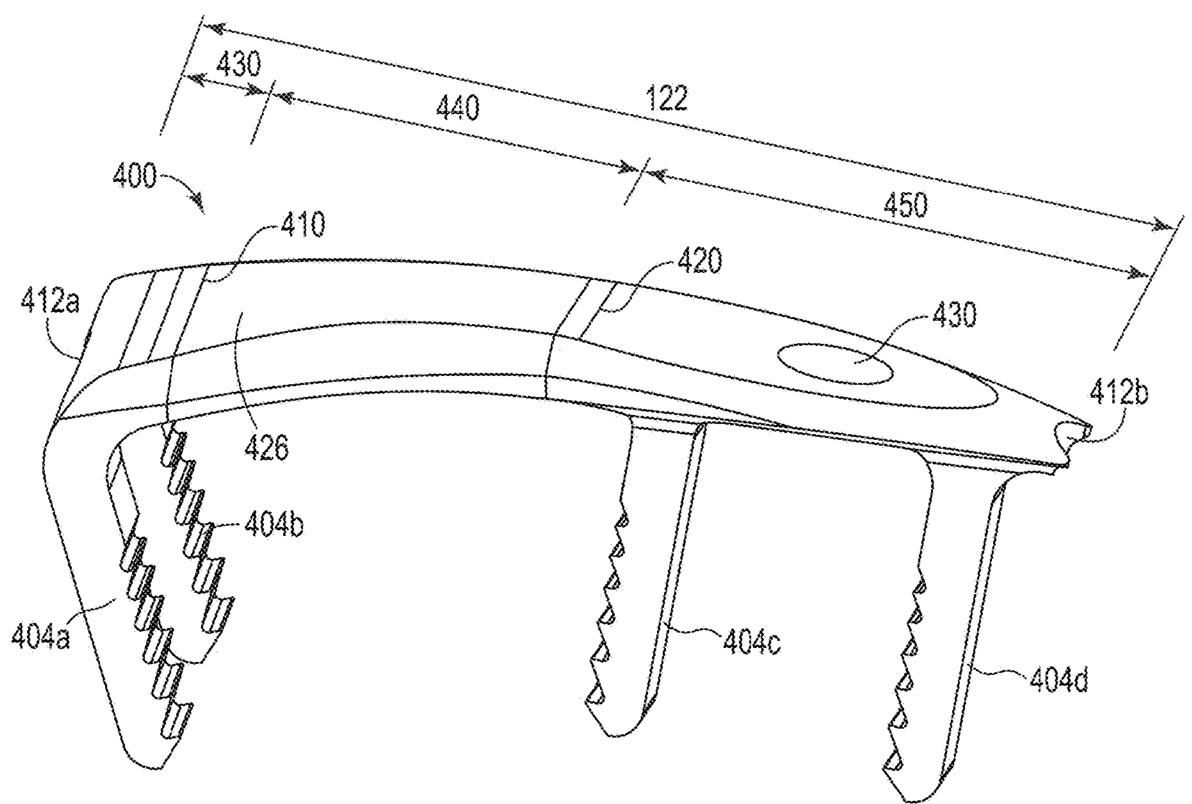
FIG. 14 illustrates a perspective view of an exemplary staple, according to one embodiment of the present disclosure.

FIGS. 12-14 illustrate another exemplary embodiment of the staple 400. The staple 400 is in a relaxed position as illustrated and described above with respect to FIGS. 6-9. The staple 400 includes legs 404*a*, 404*b*, 404*c*, 404*d*. As shown in FIG. 13, the staple 400 includes a torsional angle $\theta_6$ illustrating an angle between formed between the third and fourth legs 404*c*, 404*d* and the y-axis based on a twist and/or bend of the bridge.

Furthermore, FIGS. 12-13 illustrate various contour features 410, 420 on the top surface 426 of the staple 400. In the embodiment shown, the top surface includes a first section 430, a second section 440, and a third section 450 spanning across the length 122 of the staple 400. The first contour feature 410 illustrates one or more transition features between a first section 430 of the top surface 426 abutting the first end 412*a* and a second section 440 positioned between the first section 430 and the third section 450. The second contour feature 420 illustrates one or more transition features between the second section 440 of the top surface 426 and the third section 450 abutting the second end 412*b*.

In certain embodiments, the contour features 410, 420 can include one or more contouring techniques including a fillet or chamfer, a blended surface, a loft, a sweep, or a blend curve.

FIGS. 15-21 illustrate another example embodiment of a staple 500. The staple 500 includes a top surface 526 defining a first end section 520 abutting the first end 512*a*, a first side section 506 and a second side section 514 spanning along a length 122 of the bridge 508, a second end section 510 abutting the second end 512*b*, and a central section 522 between the first end section 520 and the second end section 510 and the first side section 506 and the second side section 514.

Figure 15:
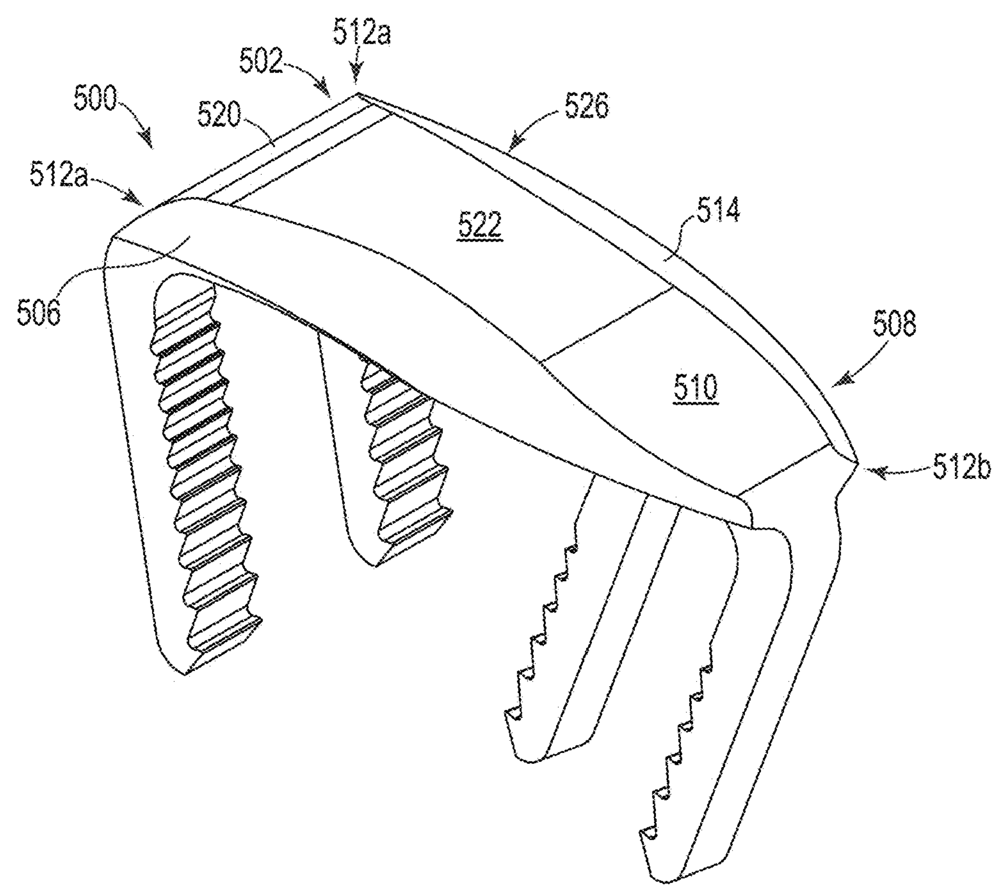
FIG. 15 illustrates a perspective view of an exemplary staple, according to one embodiment of the present disclosure.

As shown in FIG. 15, in certain embodiments, the staple 500 includes one or more transitionary features (e.g., contour features 502) between one or more sections of the top surface 526, including a transition between the first end section 520 and the central section 522, the first end section 520 and either of the first side section 506 or the second side section 514, the central section 522 and the second end section 510, or the second end section 520 and either of the first side section 506 or the second side section 514. In certain embodiments, these features can include contour features having one or more contouring techniques including a fillet or chamfer, a blended surface, a loft, a sweep, or a blend curve.

Figure 16:
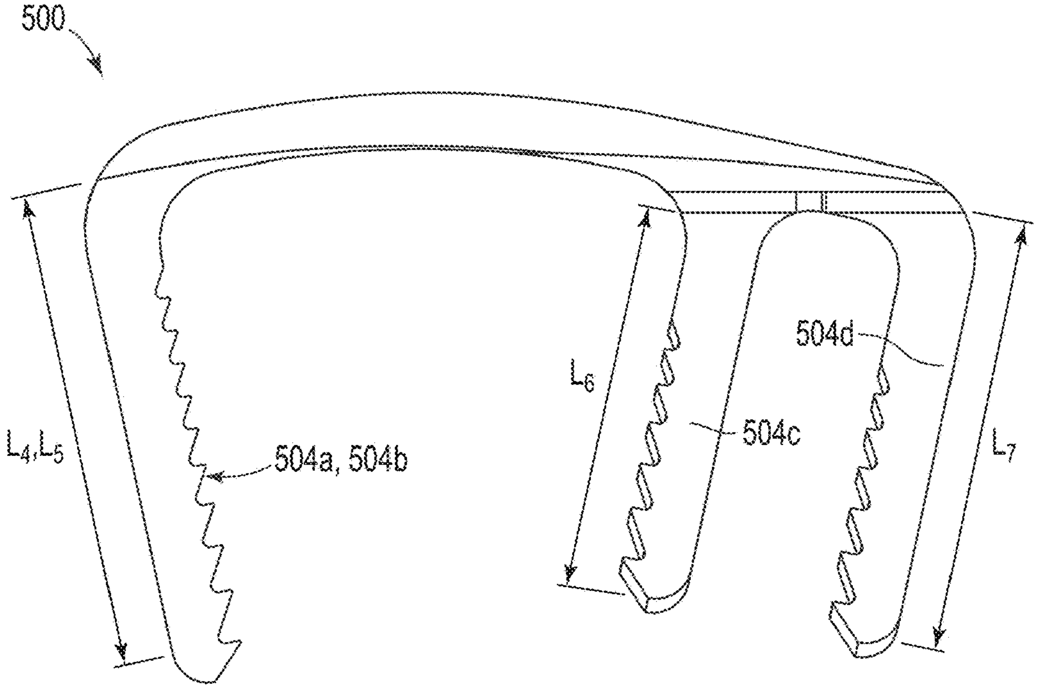
FIG. 16 illustrates a front view of the exemplary staple of FIG. 15, according to one embodiment of the present disclosure.

As shown in FIG. 16, in certain embodiments, the staple 500 includes legs 504*a*, 504*b*, 504*c*, and 504*d* having varying leg lengths $L_4$, $L_5$, $L_6$, and $L_7$. In certain embodiments, and as shown in FIG. 16, the first leg 504*a* and the second leg 504*b* may have a first leg length $L_4$ and a second leg length $L_5$ that are substantially equal. In certain embodiments, and as further shown in FIG. 16, the third leg 504*c* and the fourth leg 504*d* may have a third leg length $L_6$ and a fourth leg length $L_7$ that are not equal to the first leg length $L_4$ and the second leg length $L_5$. Furthermore, in certain embodiments, the third leg length $L_6$ and the fourth leg length $L_7$ can be equivalent or not equivalent.

Figure 17:
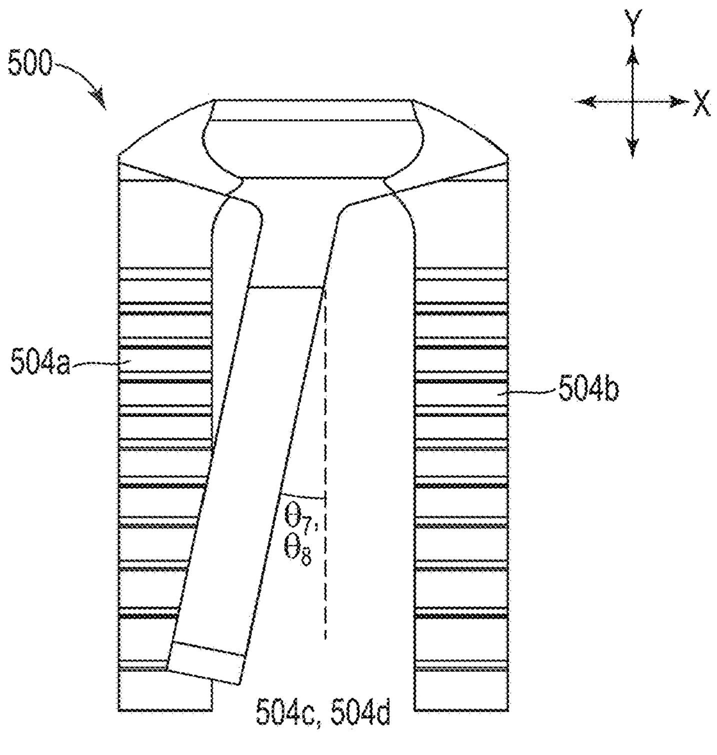
FIG. 17 illustrates a side view of the exemplary staple of FIGS. 15-16, according to one embodiment of the present disclosure.
Figure 18:
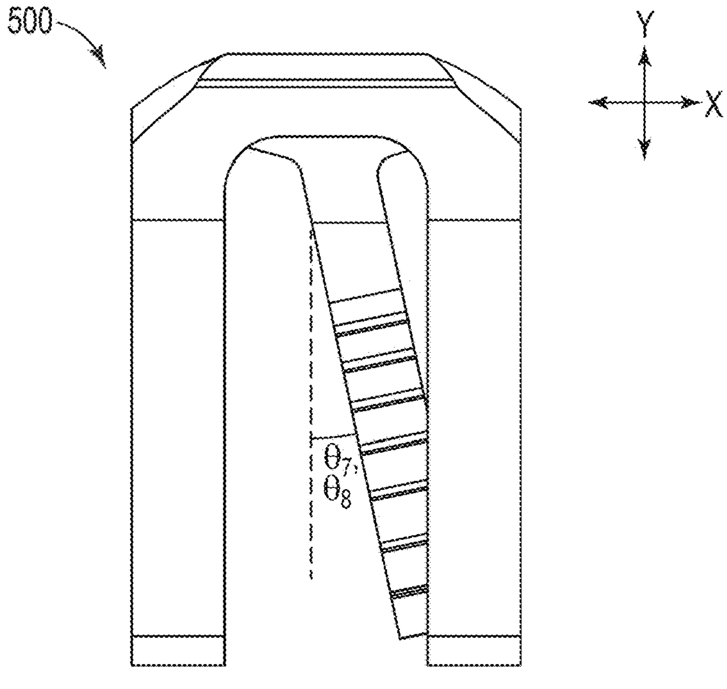
FIG. 18 illustrates a side view from the opposite side of the exemplary staple of FIG. 17, according to one embodiment of the present disclosure.
Figure 19:
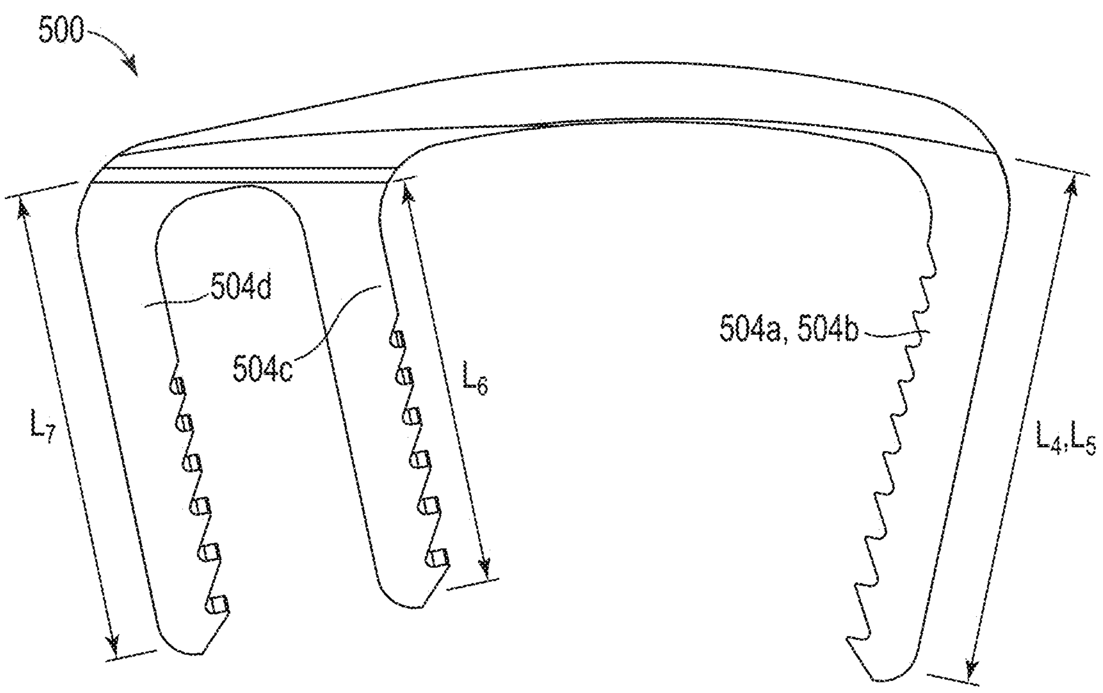
FIG. 19 illustrates a rear view of the exemplary staple of FIGS. 15-18, according to one embodiment of the present disclosure.
Figure 20:
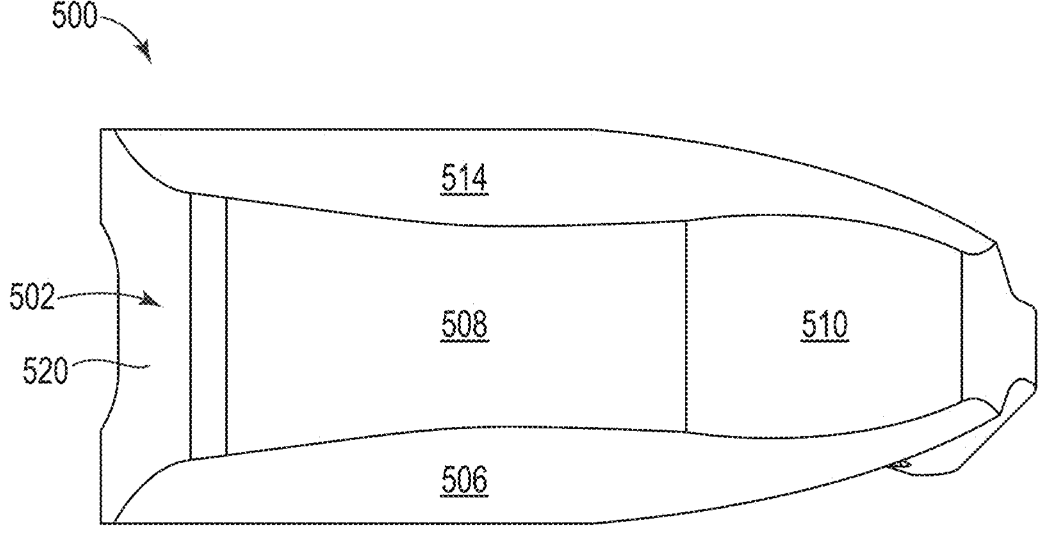
FIG. 20 illustrates a top view of the exemplary staple of FIGS. 15-19, according to one embodiment of the present disclosure.
Figure 21:
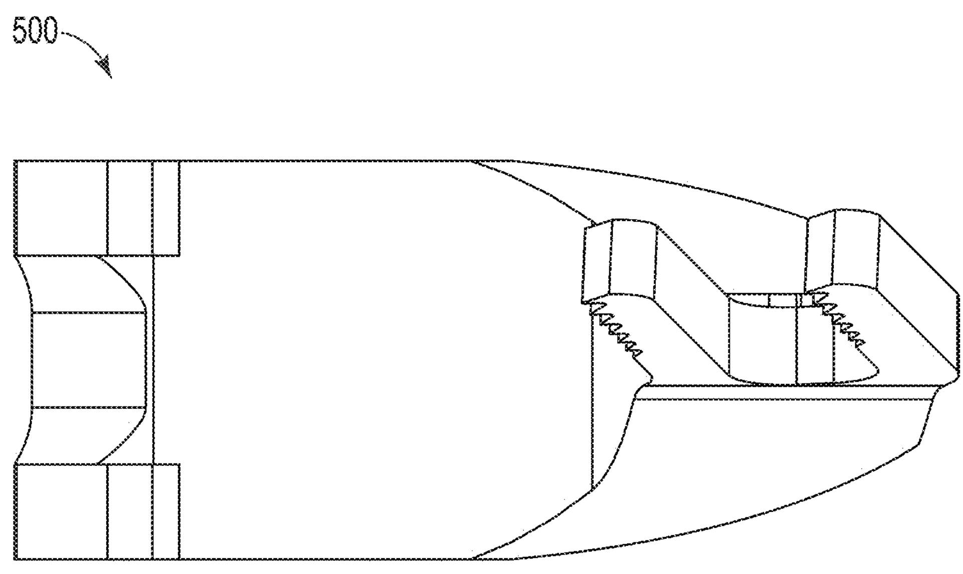
FIG. 21 illustrates a bottom perspective view of the exemplary staple of FIGS. 15-20, according to one embodiment of the present disclosure.

As shown in FIGS. 17-18, in certain embodiments, the staple 500 includes a twist resulting in torsional angles $\theta_7$ between the third leg 504*c* and the y-axis and a torsional angle $\theta_8$ between the fourth leg 504*d* and the y-axis. In certain embodiments, and as shown in FIGS. 17-18, the torsional angles $\theta_7$, $\theta_8$ are equivalent. In alternative embodiments, the torsional angles $\theta_7$, $\theta_8$ are not equivalent.

FIGS. 22-28 illustrate another exemplary embodiment of a staple 600 according to the present disclosure.

Figure 22:
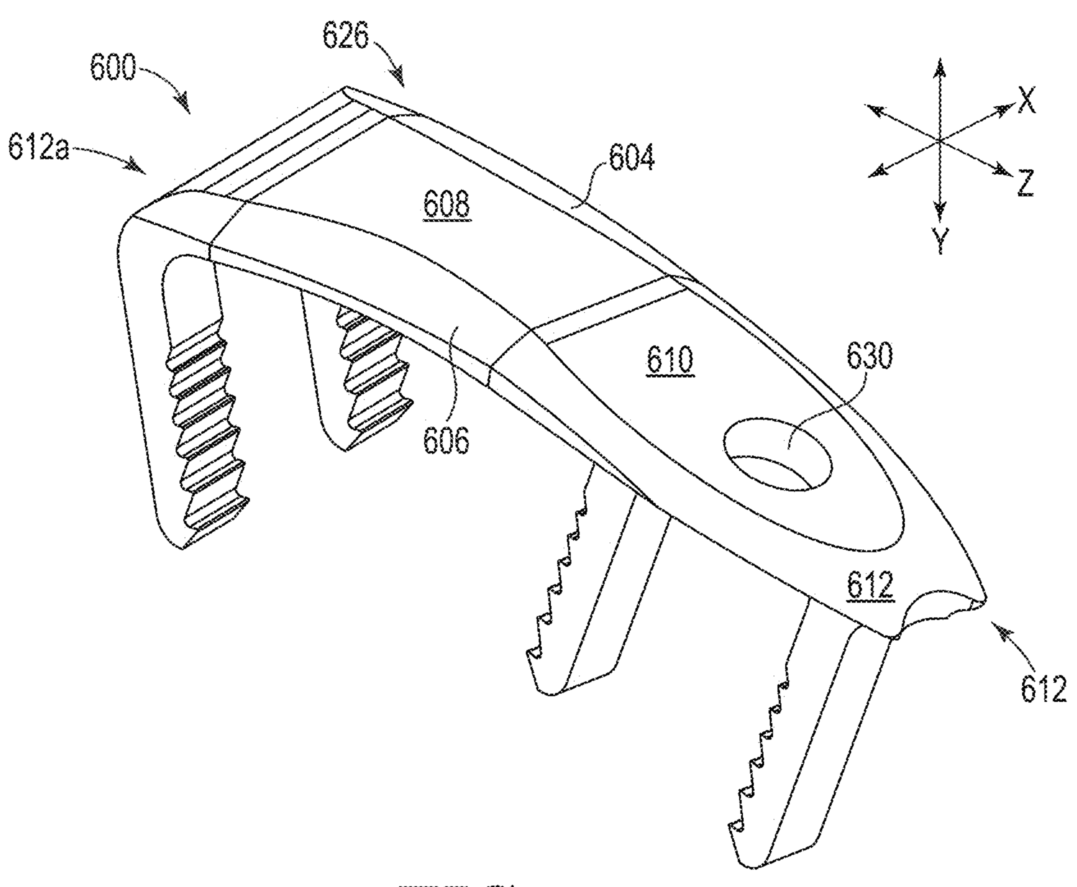
FIG. 22 illustrates a perspective view of an exemplary staple, according to one embodiment of the present disclosure.
Figure 23:
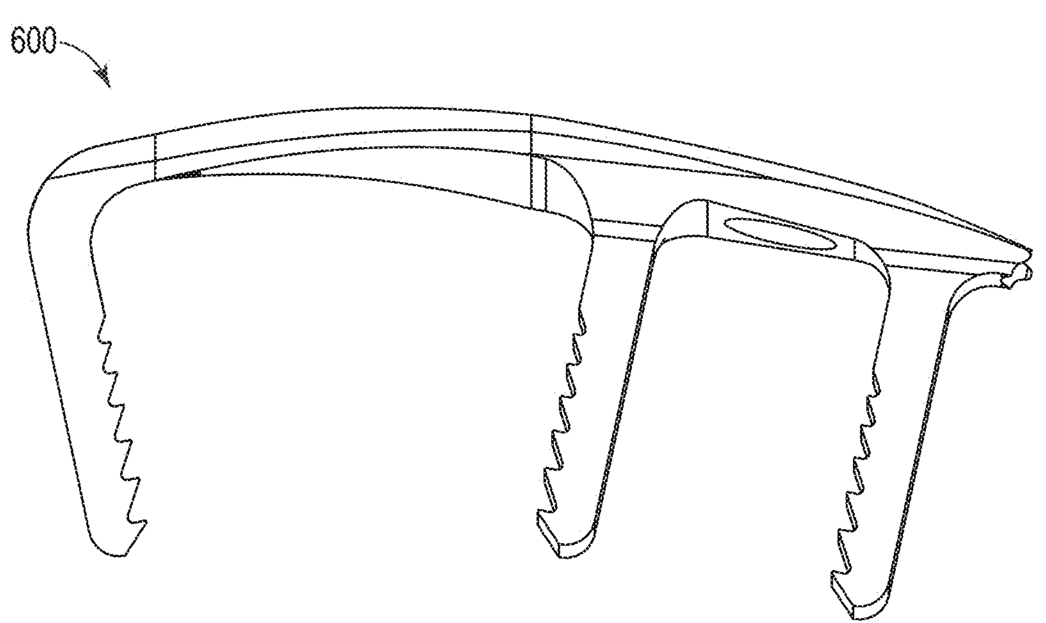
FIG. 23 illustrates a front view of the exemplary staple of FIG. 22, according to one embodiment of the present disclosure.
Figure 24:
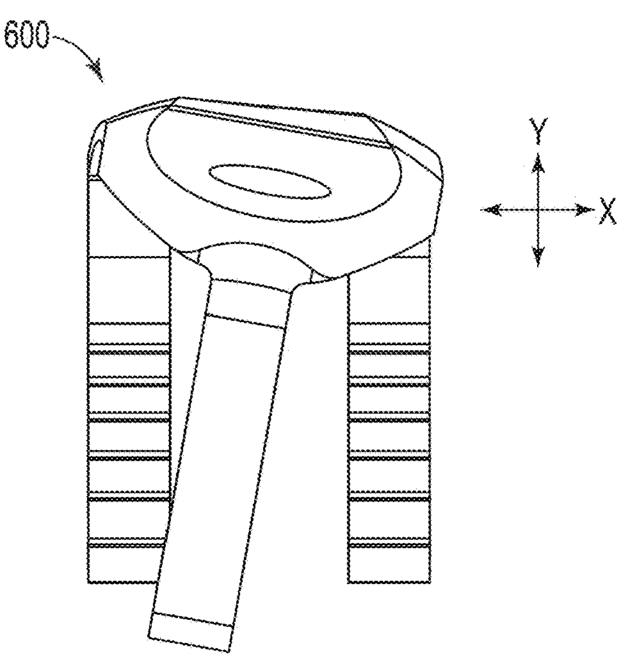
FIG. 24 illustrates a side view of the exemplary staple of FIGS. 22-23, according to one embodiment of the present disclosure.
Figure 25:
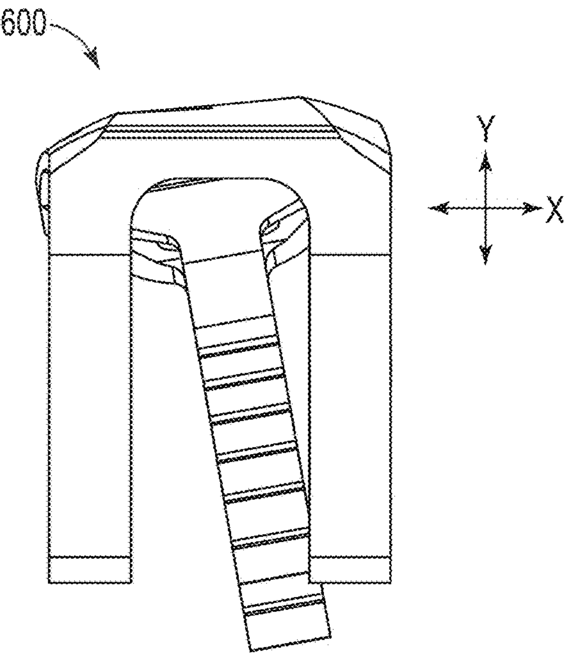
FIG. 25 illustrates a side view of opposite side of the exemplary staple of FIGS. 24, according to one embodiment of the present disclosure.
Figure 26:
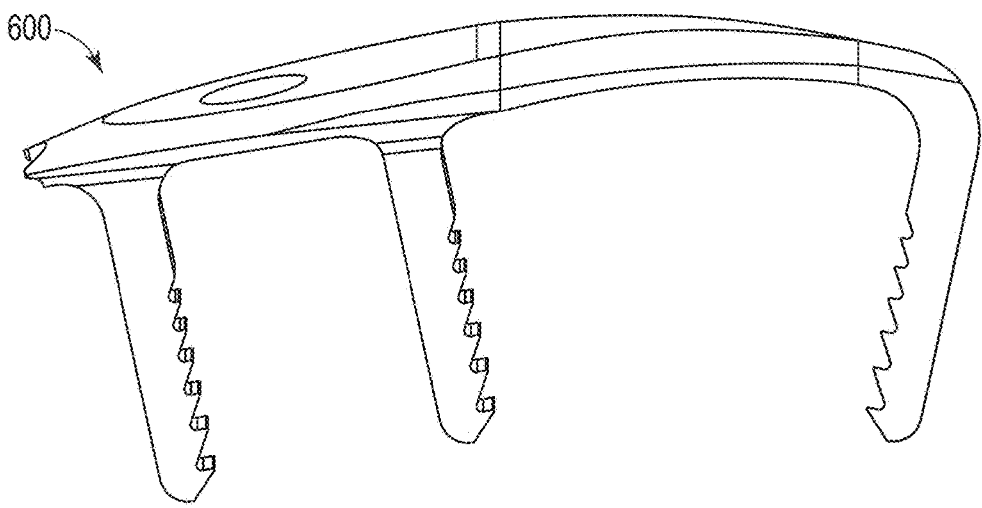
FIG. 26 illustrates a rear view of the exemplary staple of FIGS. 22-25, according to one embodiment of the present disclosure.

As shown in FIGS. 22 and 27, the staple 600 includes a top surface 626 defining various features. The top surface 626 includes a first end section 630 abutting the first end 612*a*, a second end section 650 abutting a second end 612*b*, and a central section 640 between the first end section 630 and the second end section 650.

In certain embodiments, the staple 600 includes one or more transition features between one or more sections of the top surface 626 (e.g., the first end section 630, the central section 640, and the second end section 650). The transition features include first transition portions 620, 622 between the first end section 630 and the central section 640 and one or more second transition portions 614 between the central section 640 and the second end section 650.

Furthermore, in certain embodiments the staple 600 can include one or more transition features for transitioning from a central axis 670 toward one or more edges of the staple. In certain embodiments, the first end section 630 includes a centered portion 616 with two transition portions 614, 620 and one or more transition features therebetween. In certain embodiments, the central section includes a centered portion 608 with two end portions 604, 606 and one or more transition features therebetween. In certain embodiments, the second end section 6160 includes a centered portion 610 with an end portion 624 surrounding the centered portion.

In certain embodiments, the one or more transition features can include contour features having one or more contouring techniques including a fillet or chamfer, a blended surface, a loft, a sweep, or a blend curve.

Figure 29:
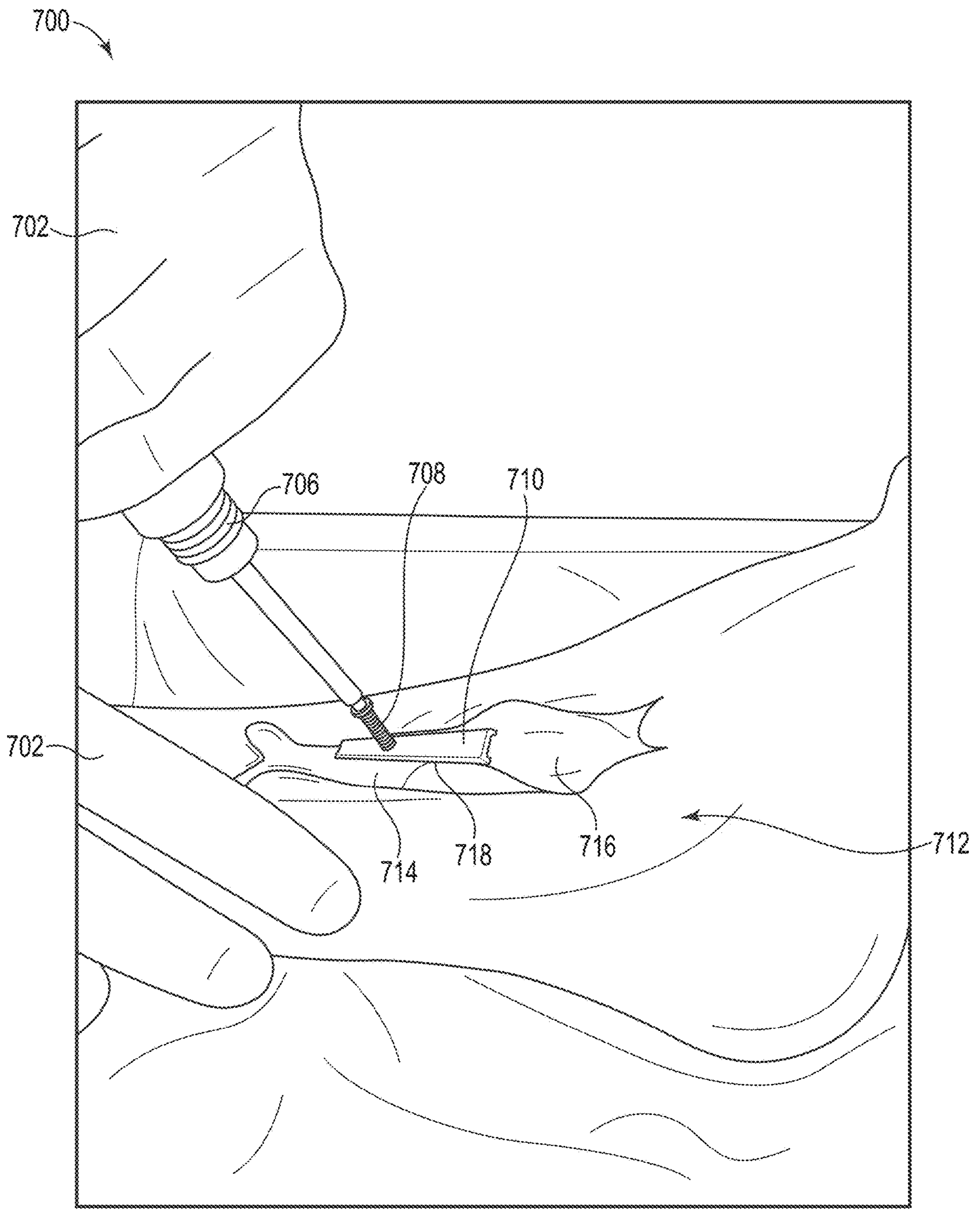
FIG. 29 illustrates a perspective view of an example surgical site where an exemplary staple is used to join one or more bones located at the ankle joint.

FIG. 29 illustrates a perspective view of an example surgical site 700 where an exemplary staple 710 is used to join one or more bones located at the ankle joint 712.

The surgical site 700 includes a surgeon 702 inserting a fastener 708 through the exemplary staple 710 using a hand tool 706 (e.g., a screwdriver) to connect one or more bones at the ankle joint 712 (e.g., the tibia 714 and the fibula 716). The exemplary staple 710 is positioned across a fracture 718 between one or more bones in the ankle joint 712 to stabilize the ankle joint and promote healing by exerting compressive forces across the fracture site to promote bone union by bringing fractured ends closer together and compressing them. Furthermore, the use of an exemplary staple 710 is desirable because it is minimally invasive and simple to remove, utilizes biocompatible materials, and can be applied rapidly.

Figure 30:
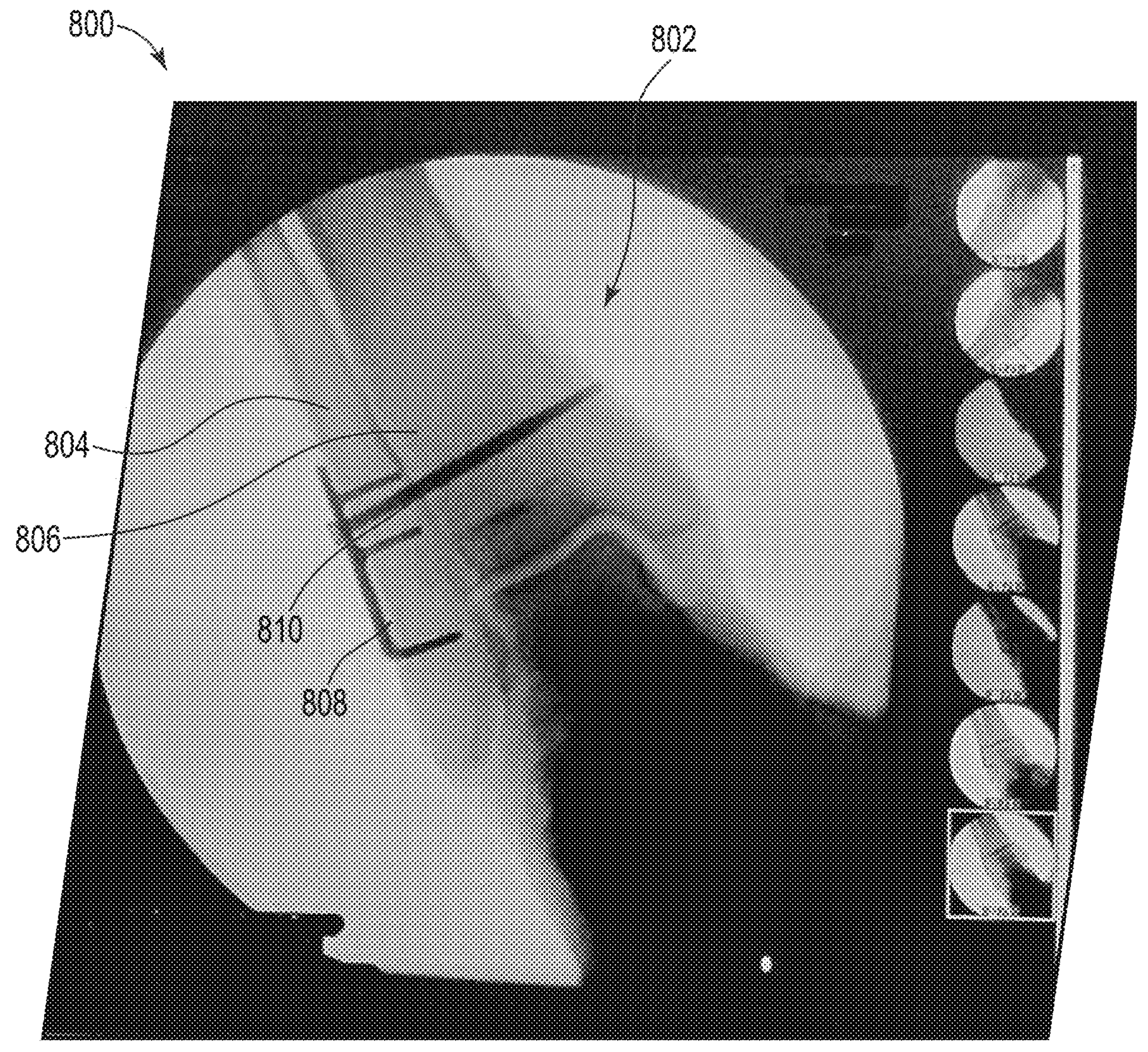
FIG. 30 illustrates a radiological image of a surgical site including an exemplary staple used to join one or more bones located at the ankle joint.

FIG. 30 illustrates a radiological image 800 of a surgical site 802 including an exemplary staple 808 used to join one or more bones located at the ankle joint.

As shown in FIG. 30, and as described in further detail above with respect to FIG. 11, the radiological image 800 illustrates a syndesmotic procedure where the staple 808 and a fastener 810 are positioned at the surgical site 802 (e.g., the ankle joint). The staple 808 is positioned on a lateral side of the ankle joint at the fibula, and the fastener 810 connects the fibula 804 to the tibia 806 to improve stability of the ankle joint and surrounding soft tissue.

Figure 31:
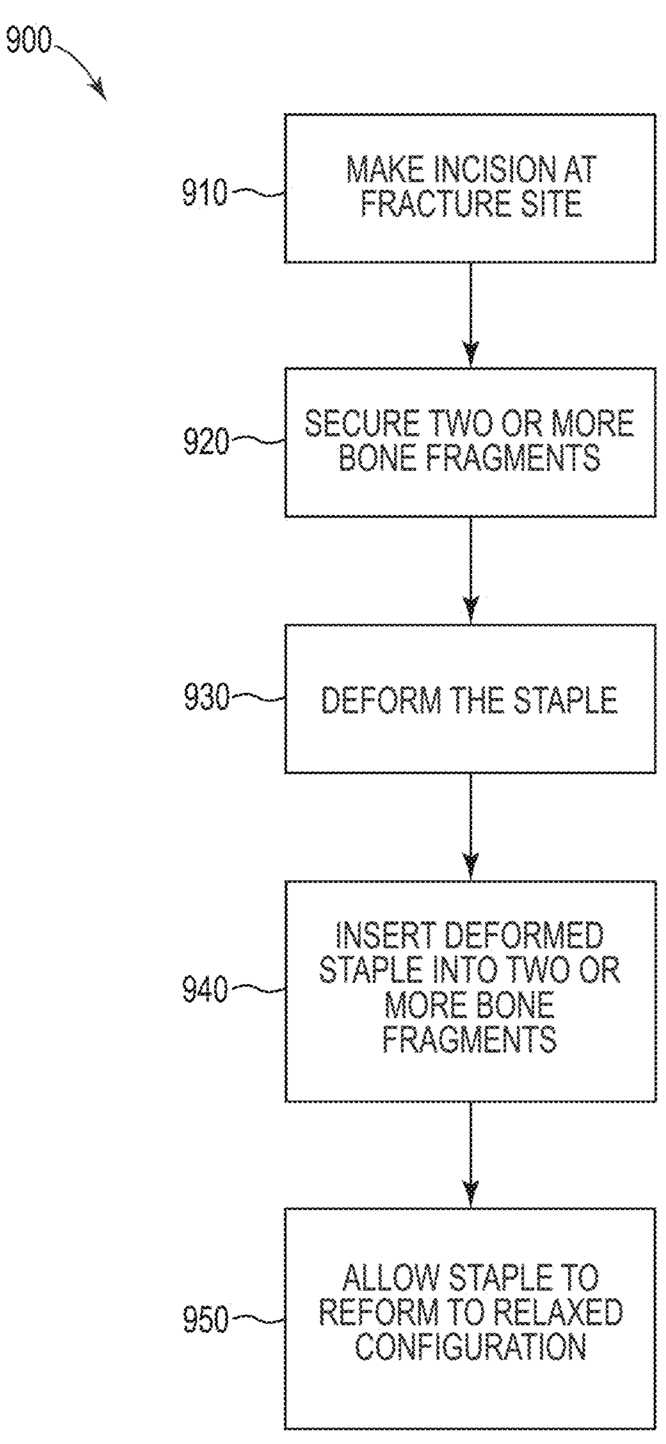
FIG. 31 illustrates a method flow diagram of a method for connecting two or more bone fragments at an ankle joint.

FIG. 31 illustrates a method flow diagram of a method 900 for connecting two or more bone fragments at an ankle joint.

The method includes a step 910 of making an incision at a fracture site where one or more bones have been fractured.

The method includes a step 920 of securing two or more bone fragments together. In certain embodiments, the one or more bone fragments are secured in a desired position using one or more surgical clamping instruments. The one or more surgical clamping instruments can include, by non-limiting example, any tool used to grasp, hold, or compress tissues, blood vessels, or other anatomical structures during surgical procedures. In certain embodiments, the one or more surgical clamping tools include at least one of hemostatic forceps, tissue forceps, bulldog clamps, Babcock forceps, allis tissue forceps, and Lane bone holding forceps.

The method 900 includes a step 930 of deforming the staple to an active configuration. As will be understood, in some embodiments, exemplary staples discussed herein may be pre-packaged for surgery in an inserted that holds (or partially holds) the staple in a deformed/active configuration such that a surgeon does not need to deform or fully deform the staple.

The method 900 includes a step 940 of inserting the deformed staple into two or more bone fragments. In certain embodiments, the deformed staple in the active configuration is inserted into the two or more bone fragments using one or more screws. In certain embodiments, step 940 further includes fastening the one or more screws through one or more apertures in the bridge to the patient. As will be understood, prior to inserting the legs of the deformed staple, the surgeon may pre-drill holes for one or more of the legs of the staple and/or may insert the staple legs by impact.

The method 900 includes a step 950 of allowing the staple to reform to a relaxed configuration.

In certain embodiments, the method 900 further includes suturing the incision and inserting a fixation device (e.g., screw, nail, suture button, etc.) through a hole in the staple and through the fibula, tibia, or both.

Having thus described the present disclosure in detail, it is to be appreciated and will be apparent to those skilled in the art that many physical changes, only a few of which are exemplified in the detailed description here, could be made without altering the concepts and principles embodied therein.

The present embodiments and optional configurations are therefore to be considered in all respects as exemplary and/or illustrative and not restrictive, the scope of the present devices, processes, methods, and innovations being indicated by the appended claims rather than by the foregoing description, and all alternate embodiments and changes to this embodiment which come within the meaning and range of equivalency of said claims are therefore to be embraced therein.

The invention claimed is:

1. A staple comprising:
- a first leg and a second leg connected substantially in parallel to a bridge at a first end; and
- a third leg and a fourth leg connected to the bridge in line along a central axis between the first leg and the second leg and spanning a length of the bridge, wherein:
  - the staple is deformable from a relaxed position to an active position;
  - in the relaxed position:
    - the first leg and the second leg are positioned at a first bend angle relative to a y-axis;
    - the third leg is positioned at a second bend angle relative to the y-axis; and
    - the bridge comprises a twist angle, thereby positioning:
      - the third leg at a first torsion angle relative to the y-axis; and
      - the fourth leg at a second torsion angle relative to the y-axis; and
  - in the active position, the first bend angle, the second bend angle, the first torsion angle, and the second torsion angle are approximately 0 degrees.

2. The staple of claim 1, wherein the staple comprises nitinol.

3. The staple of claim 1, wherein the staple is configured for:
- implantation within bony fragments of a patient in the active position; and
- upon the implantation, the staple moves from the active position to the relaxed position thereby providing multiplanar compression to the bony fragments.

4. The staple of claim 3, wherein the magnitude of compression is relative to the first and second bend angles and the twist angle.

5. The staple of claim 4, wherein the twist angle is approximately 10 degrees.

6. The staple of claim 5, wherein the staple defines a hole through the bridge between the third leg and the fourth leg for receiving a fixation device.

7. The staple of claim 6, wherein:
- the bridge comprises:
  - a first thickness between the third leg and the fourth leg, proximate the hole; and
  - a second thickness between the third leg and the first and second legs; and
- the first thickness is greater than the second thickness.

8. The staple of claim 7, wherein one or more of the first leg, the second leg, the third leg, and the fourth leg comprise one or more teeth.

9. The staple of claim 8, wherein each of the first leg, the second leg, the third leg, and the fourth leg comprise one or more teeth.

10. The staple of claim 9, wherein each tooth comprises a tooth angle measuring between 45-60 degrees.

11. The staple of claim 10, wherein the bridge comprises a variable cross-sectional width.

* * * * *